(12) United States Patent
Beauchamp et al.

(10) Patent No.: US 8,153,368 B2
(45) Date of Patent: Apr. 10, 2012

(54) FOUR-JOINTED BOX (FJX1) IN CANCER DIAGNOSIS AND TREATMENT

(75) Inventors: R. Daniel Beauchamp, Nashville, TN (US); Bonnie J. LaFleur, Salt Lake City, UT (US); Nipun B. Merchant, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 70 days.

(21) Appl. No.: 12/146,167

(22) Filed: Jun. 25, 2008

(65) Prior Publication Data

US 2009/0232813 A1 Sep. 17, 2009

Related U.S. Application Data

(60) Provisional application No. 60/946,071, filed on Jun. 25, 2007.

(51) Int. Cl.
*C12Q 1/68* (2006.01)
(52) U.S. Cl. ......................................... 435/6.1
(58) Field of Classification Search .................. None
See application file for complete search history.

(56) References Cited

U.S. PATENT DOCUMENTS

2003/0232350 A1* 12/2003 Afar et al. ......................... 435/6

OTHER PUBLICATIONS

Yerushalmi et al (Gene, 2001, vol. 265, pp. 55-60).*
Caillou et al (Journal of Clinical Endocrinology and Metabolism, 2001, vol. 86, pp. 3351-3351).*
Lewin B, ed, 1983, Genes, John Wiley & Sons, NY, p. 181,428.*
Bowie (Science, 1990, 257:1306-1310).*
Burgess et al, 1990, J Cell Biol, 111: 2129-2138.*
Schmid S et al, 2001 (J comparative Neurology, 430(2): 160-71).*
Conner et al, 1996 (Mol Brain Res, 42: 1-17).*
Guate et al, 1999 (BJU Internatl, 84: 495-502).*
Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Ashery-Padan et al., "Fjx1, the murine homologue of the Drosophila four-jointed gene, codes for a putative secreted protein expressed in restricted domains of the developing and adult brain," *Mech. Dev.*, 80 (2): 213-217, 1999.
Ishikawa et al., "Four-jointed Is a Gogli Kinase That Phosphorylates a Subset of Cadherin Domains," *Science*, 321 (5887): 401-404, 2008.
Kakiuchi et al., "Genome-Wide Analysis of Organ-Preferential Metastasis of Human Small Cell Lung Cancer in Mice," *Mol. Canc. Research*, 1:485-499, 2003.
Oyan et al., "cDNA microarray analysis of non-selected cases of acute myeloid leukemia demonstrates distinct clustering independent of cytogenetic abberations and consistent with morphological signs of differentiation," *Int. J. of Oncology*, 28: 1065-1080, 2006.
Probst et al., "The rodent Four-jointed ortholog Fjx1 regulates dendrite extension," *Dev. Biol*, 312(1): 461-470, 2007.
Radtke and Clevers, "Self-renewal and cancer of the gut: two sides of a coin," *Science*, 307 (5717): 1904-1909, 2005.
Rock et al., "Expression of mouse dchs1, fjx1, and fat-j suggests conservation of the planar cell polarity pathway identified in Dosophila," *Dev. Dyn.*, 234 (3): 747-755, 2005.
Rock et al., "Fjx1: a notch-inducible secreted ligand with specific binding sites in developing mouse embryos and adult brain," *Dev. Dyn.*, 234 (3): 602-612, 2005.
Saburi et al., "Los of Fat4 disrupts PCP signaling and oriented cell division and leads to cystic kidney disease," *Nat. Genet,.* 40 (8): 1010-1015, 2008.
Snijders et al., "Rare amplicons implicate frequent deregulation of cell fate specification pathways in oral squamous cell carcinoma," *Oncogene*, 24 (26): 4232-4242, 2005.
Van Es et al., "Notch and Wnt inhibitors as potential new drugs for intestinal neoplastic disease," *Trends Mol. Med.*, 11 (11): 496-502, 2005.

* cited by examiner

*Primary Examiner* — Sean Aeder
(74) *Attorney, Agent, or Firm* — Fulbright & Jaworski

(57) ABSTRACT

The present invention relates to a new tumor suppressor, designated FJX1. Also described are diagnostic, prognostic and therapeutic uses of the FJX1 protein and the FJX1 gene, alone or in combination with traditional cancer therapies.

6 Claims, 24 Drawing Sheets

SEQUENCE LISTING

<160> NUMBER OF SEQ ID NOS: 4

<210> SEQ ID NO 1
<211> LENGTH: 450
<212> TYPE: PRT
<213> ORGANISM: Mus musculus

<400> SEQUENCE: 1

```
Met Gly Arg Lys Met Arg Gly Ala Ala Ala Ala Gly Leu Trp Leu
1               5                   10                  15

Leu Ala Leu Ser Ser Leu Leu Thr Leu Trp Gly Gly Leu Leu Pro Pro
                20                  25                  30

Arg Thr Glu Leu Pro Ala Ser Arg Pro Pro Glu Asp Arg Leu Pro Pro
                35                  40                  45

His Pro Ile Gln Ser Gly Gly Pro Ala Pro Glu Pro Arg Phe Pro Leu
            50                  55                  60

Pro Pro Pro Leu Val Trp Asp Ala Arg Gly Gly Ser Leu Lys Thr Phe
65                  70                  75                  80

Arg Ala Leu Leu Thr Leu Ala Ala Gly Ala Asp Asn Pro Pro Arg Arg
                85                  90                  95

His Gln Asp Asp Arg Gly Arg His Glu Pro Ser Gly Leu Ser Trp Pro
            100                 105                 110

Glu Glu Arg Arg Ala Val His Gly Gly Val Phe Trp Ser Arg Gly Leu
        115                 120                 125

Glu Glu Gln Val Pro Arg Gly Phe Ser Glu Ala Gln Ala Ala Ala Trp
    130                 135                 140

Leu Glu Val Ala Arg Gly Ala Arg Val Val Ala Leu Asp Arg Gly Gly
145                 150                 155                 160

Cys Gly Arg Ser Ser Asn Arg Leu Ala Arg Phe Ala Asp Gly Thr Arg
                165                 170                 175

Ala Cys Val Arg Tyr Gly Ile Asn Pro Glu Gln Ile Gln Gly Glu Ala
            180                 185                 190

Leu Ser Tyr Tyr Leu Ala Arg Leu Leu Gly Leu Gln Arg His Val Pro
        195                 200                 205

Pro Leu Ala Leu Ala Arg Val Glu Ala Arg Gly Ala Gln Trp Val Gln
    210                 215                 220

Val Gln Glu Glu Leu Arg Thr Ala His Trp Thr Glu Gly Ser Val Val
225                 230                 235                 240

Ser Leu Thr Arg Trp Leu Pro Asn Leu Thr Asp Val Val Pro Glu
                245                 250                 255

Pro Trp Arg Ser Glu Asp Gly Arg Leu Arg Pro Leu Arg Asp Ala Gly
            260                 265                 270

Gly Glu Leu Thr Asn Leu Ser Gln Ala Glu Leu Val Asp Leu Val Gln
        275                 280                 285

Trp Thr Asp Leu Ile Leu Phe Asp Tyr Leu Thr Ala Asn Phe Asp Arg
    290                 295                 300

Leu Val Ser Asn Leu Phe Ser Leu Gln Trp Asp Pro Arg Val Met His
305                 310                 315                 320

Arg Ala Thr Ser Asn Leu His Arg Gly Pro Gly Gly Ala Leu Val Phe
                325                 330                 335

Leu Asp Asn Glu Ala Gly Leu Val His Gly Tyr Arg Val Ala Gly Met
            340                 345                 350

Trp Asp Lys Tyr Asn Glu Pro Leu Leu Gln Ser Val Cys Val Phe Arg
        355                 360                 365
```

```
Glu Arg Thr Ala Arg Arg Val Leu Glu Leu His Arg Gly Gln Asp Ala
    370                 375                 380

Ala Ala Arg Leu Leu Arg Leu Tyr Ser Arg His Glu Pro Arg Phe Pro
385                 390                 395                 400

Glu Leu Ala Glu Leu Ser Glu Pro His Ala Gln Leu Leu Gln Arg Arg
                405                 410                 415

Leu Asp Phe Leu Ala Lys His Ile Leu His Cys Lys Ala Lys Tyr Gly
            420                 425                 430

Arg Arg Pro Gly Asp Leu Ile Thr Leu Arg Gly Arg Glu Gly Leu Gly
        435                 440                 445

Tyr Glu
    450

<210> SEQ ID NO 2
<211> LENGTH: 2367
<212> TYPE: DNA
<213> ORGANISM: Homo sapiens

<400> SEQUENCE: 2
gcggccgcga tggggccgaa gcgcccgaag ccccggagcc acaaactgc cgggcccgcc         60 tcgccgccgg gacccgggtg cctgggctcg gcttgaagcg gcggcggcgc accggcacag       120
ccgcgggagc atgggcagga ggatgcgggg cgccgccgcc accgcgggc tctggctgct       180 ggcgctgggc tcgctgctgg cgctgtgggg agggctcctg ccgccgcgga ccgagctgcc       240
cgcctcccgg ccgcccgaag accgactccc acggcgcccg gccggagcg gcggccccgc       300 gcccgcgcct cgcttccctc tgccccgcc cctggcgtgg gacgcccgcg gcggctccct       360
gaaaactttc cgggcgctgc tcaccctggc ggccggcgcg gacggcccgc ccggcagtc       420 ccggagcgag cccaggtggc acgtgtcagc caggcagccc cggccggagg agagcgccgc       480
ggtgcacggg ggcgtcttct ggagccgcgg cctggaggag caggtgcccc gggcttttc       540 ggaggcccag gcggcggcgt ggctggaggc ggctcgcggc gcccggatgg tggccctgga       600
gcgcgggggt tgcgggcgca gctccaaccg actggcccgt tttgccgacg caccgcgc       660 ctgcgtgcgc tacggcatca acccggagca gattcagggc gaggccctgt cttactatct       720
ggcgcgcctg ctgggcctcc agcgccacgt gccgccgctg cactggctc gggtggaggc       780 tcggggcgcg cagtgggcgc aggtgcagga ggagctgcgc gctgcgcact ggaccgaggg       840
cagcgtggtg agcctgacac gctggctgcc caacctcacg gacgtggtgg tgcccgcgcc       900
ctggcgctcg gaggacggcc gtctgcgccc cctccgggat gccgggggtg agctggccaa       960
cctcagccag gcggagctgg tggacctagt acaatggacc gacttaatcc ttttcgacta      1020
cctgacggcc aacttcgacc ggctcgtaag caacctcttc agcctgcagt gggacccgcg      1080
cgtcatgcag cgtgccacca gcaacctgca ccgcggtccg gcggggcgc tggtctttct      1140 ggacaatgag gcgggcttgg tgcacggcta ccgggtagca ggcatgtggg acaagtataa      1200
cgagccgctg ttgcagtcag tgtgcgtgtt ccgcgagcgg accgcgcggc gcgtcctgga      1260
gctgcaccgc ggacaggacg ccgcggcccg gctgctgcgc ctctaccggc gccacgagcc      1320
tcgcttcccc gagctggccg ccttgcaga cccccacgct cagctgctac agcgccgcct      1380
cgacttcctc gccaagcaca ttttgcactg taaggccaag tacggccgcc ggtctgggac      1440
ttagtgtcac cggaggaaaa agagagagat ctggggctgg ggtatggatg atgggggaa      1500 gggcggtcgc ctctgccact gtcagggacc agccggccaa cgcccaccg caaaggtgtc      1560 taaaaacttc agcttttcac ccacctgccc ctttctttca atcccacgct gtttcctttc      1620
```

```
aaagttctgg gaggacgaac tcaccgaggc gagaagtgta acattctctc cacccagctt    1680
ataaaaggat tctttactgt gccagcacgg ggattggatc cgaagaaact ggctactggg    1740
gtttggcccc cgagtggccg tccctgtggg agatgcaccc cattcttggg cccccctcat    1800
tccctttccg aaaaaggaaa acttgcgttt gagccgttga gctaattctg caattttcta    1860
ccaaacagag cgctggtggc cccggagcag ggctgtgaca ttggctggtg gagcccttc     1920 ctgtgttctc cctttgttcc agcgccgcga tggtgagatc actgttccaa gcaggggac    1980 ggctcgcgat aggacaaaga gagcaggacc tccagactct ggggagccct gcagaccttg    2040
acaatttgcc tgactcattc ctgacctctt gtcattttgg cctgaaggct acaaattcag    2100
ggtcagctgt atgcactaag tcaaataatg aatttcttcc tccctctcgc aaccgaccaa    2160
aattttgaca acgatgatgt tcaccagaag gaaaaaaaaa tcagttttat gcactttatt    2220
ttgttttgat tttcattttt tattaagaaa aaatttattt ttacagaatt taccttctct    2280
gtatatatgt gcataaagtg tggtgtaaat atactaaaca aacttatatt tcaataaaag    2340
ggagtttaaa atttaaaaaa aaaaaaa                                        2367

<210> SEQ ID NO 3
<211> LENGTH: 31
<212> TYPE: DNA
<213> ORGANISM: Artificial
<220> FEATURE:
<223> OTHER INFORMATION: Synthetic primer

<400> SEQUENCE: 3
gatcgaattc gtgcacgggg gcgtcttctg g                                      31

<210> SEQ ID NO 4
<211> LENGTH: 35
<212> TYPE: DNA
<213> ORGANISM: Artificial
<220> FEATURE:
<223> OTHER INFORMATION: Synthetic primer

<400> SEQUENCE: 4
gatcgtcgac ctcccggtga cactaagtcc cagac                                  35
```

FOUR-JOINTED BOX (FJX1) IN CANCER DIAGNOSIS AND TREATMENT

This application claims benefit of priority to U.S. Provisional Application Ser. No. 60/946,071, filed Jun. 25, 2007, the entire contents of which are hereby incorporated by reference.

This invention was made with government support under grant nos. P50 CA95103 & ROI CA069457, and grant no. ROI DK052334, awarded by the National Cancer Institute and the National Institute of Diabetes and Digestive and Kidney Diseases, respectively. The government has certain rights in the invention.

BACKGROUND OF THE INVENTION

I. Field of the Invention

The present invention relates to the fields of oncology, genetics and molecular biology. More particular the invention relates to the overexpression of FJX1 in colon cancer cells, its use as a diagnostic and prognostic marker, and its targeting in colon cancer therapy.

II. Related Art

Colorectal carcinoma (CRC) is the second leading cause of cancer-related deaths in the United States. Currently, it is estimated that there will be approximately 150,000 new cases of CRC and over 56,000 people will die of this disease annually (Jemal et al., 2005; Jemal et al., 2006). While localized tumor growth may cause significant organ dysfunction and even death, metastases cause the vast majority (~90%) of human cancer deaths (Hanahan and Weinberg, 2000). The ability to metastasize is linked with the ability of cancer cells to invade adjacent tissues, to gain access to vascular or lymphatic channels and to survive their transit so that they may extravasate, then reside and colonize another organ or tissue. Cancer cells acquire the capacity of invasion and metastasis, ultimately due to the interplay of activated oncogenes and loss of tumor suppressor function, but the downstream requisite effectors of these interactions in the regulation of invasiveness and metastasis are incompletely understood. Most lethal cancers are carcinomas; tumors that originate from epithelial cells. Normal epithelial cells exist as well-ordered, immobile, polarized units with controlled and structured cell-cell and cell-matrix junctions. Invasiveness and metastasis in carcinomas involve alterations in the function of cell adhesion molecules such as cadherins and integrins and alterations in expression and activation of extracellular proteases and their inhibitors. Identification of specific effectors of invasiveness and metastasis will provide opportunities for enhanced intervention strategies.

Notch signaling, intestinal development and colorectal cancer. Notch signaling is a highly conserved mechanism of cell-cell communication and regulation of differentiation, proliferation and apoptotic programs during organogenesis and morphogenesis (reviewed in Artavanis-Tsakonas et al., 1999; Wilson and Radtke, 2006). Notch signaling is activated when Delta1-like or Jagged ligands interact with Notch receptors culminating in cleavage of Notch by a presenilin-dependent activity called γ-secretase and release of the Notch Intracellular Domain (NICD). NICD is translocated to the nucleus where it binds to the DNA binding protein RBP-J (also known as CSL (CBF1-human, Su(H)-fly, Lag1-worm) where it displaces RBP-J corepressors and enables transcription of additional transcription factors related to *Drosophila* hairy and enhancer of split (Hes1, 5, 7 or HERP 1, 2, 3; also known as Hey/Hesr/HRT/CHF/gridlock (FIG. 1). The Hes-related proteins then repress expression of target genes such as Math1, neurogenin (ngn) and Achaete-scute. intera Notch, Wnt and TGF-β/BMP/Smad signaling in intestinal epithelium. Recent exciting observations have been made regarding the role of Notch in the maintenance of proliferating crypt cells in the normal intestinal epithelium. Regulated Notch signaling in the intestinal crypt is necessary for proper lineage differentiation of intestinal epithelial cells (reviewed in (van Es and Clevers, 2005; Wilson and Radtke, 2006). Activation of Notch signaling in the intestinal epithelium amplifies the proliferating enterocyte progenitor pool and inhibits differentiation (Fre et al., 2005) while inhibition of Notch signaling shuts down crypt progenitor cell proliferation results in goblet cell differentiation (van Es and Clevers, 2005). Inhibition of Notch signaling by pharmacologically blocking γ-secretase activity resulted in induction of Math1 and differentiation into a post-mitotic goblet cell lineage; this phenocopies conditional intestinal Rbp-j gene silencing (van Es and Clevers, 2005). Hes1−/− mice die during embryonic development due to severe neurological abnormalities, but specifically the intestines of the Hes1−/− mice exhibit increased mucous secreting and enteroendocrine cells with relatively fewer absorptive enterocytes (Jensen et al., 2000). Wnt and Notch signaling pathways are simultaneously active in the intestinal crypt of normal epithelium Furthermore, Notch activation is evident throughout the abnormal epithelium of adenomas in ApcMin/+mice (Vooijs et al., 2007) and inhibition of Notch signaling with a γ-secretase inhibitor induces goblet cell differentiation in the adenomas. Thus, Notch signaling is important for normal intestinal epithelial cell proliferation and maintenance of normal distribution of absorptive enterocytes and secretory cells; and when disrupted, differentiation down a secretory pathway and growth arrest occur. Notch signaling with high levels of HES1 and repressed Math1 are necessary for maintaining the proliferative state in colon adenoma cells arising from Wnt signaling activation.

Increased expression of Notch mRNA and proteins has been reported in colon and pancreatic cancers and Jagged is overexpressed in a subset of pancreatic cancers (reviewed in Leong and Karsan, 2006). IKKA associates with specific Notch target gene promoters, releasing SMRT and leading to increased transcription of hes1, hes5, herp2/hrt1 in human colon cancers (Fernandez-Majada et al., 2007). Recent evidence supports important interactions of TGF-β and BMP signaling pathways with Notch and these interactions may have important consequences in development and cancer (Kluppel and Wrana, 2005; Zavadil et al., 2004). Smad3 interacts directly with NICD to activate hes-1 and inhibit myogenic regulatory factors such as MyoD, thus inhibiting differentiation in muscle. Notch is required for BMP mediated inhibition of myogenic differentiation and NICD directly interacts with Smad1 in response to BMP receptor activation. Notch and BMP synergize to activate the hes-related Herp2 in endothelial cells (ECs). When ECs without cell-cell contact are exposed to BMP, Smad1 phosphorylation leads to expression of Id1, an activator of EC migration. On contact with cells expressing Jagged or Delta, Notch is activated leading to synergistic activation of Herp2 which promotes degradation of Id1, thus Herp2 is a negative regulator of migration (Kluppel and Wrana, 2005). Zavadil et al. (2004) recently reported that TGF-β-induced EMT in mouse kidney tubular epithelial cells was accompanied by activation of Hey1 and delayed expression of Jagged 1 in a Smad3 dependent manner. Induction of Hey1 and Jagged were required for TGF-β induced EMT in epithelial cells from kidney, breast and skin. Therefore, normal regulation of Notch, Wnt and TGF-β/BMP signaling are necessary for normal crypt progenitor cell maintenance, proliferation and differentiation. Furthermore, even in the presence of active Wnt signaling, Notch signaling is required for maintenance of the proliferative enterocyte phenotype.

Despite this information, the potential role of Notch, Wnt and TGF-β/BMP/Smad signaling in normal cell development as well as in colorectal cancer cell behavior and tumor progression, remains unclear.

SUMMARY OF THE INVENTION

Thus, in accordance with the present invention, there is provided a method of diagnosing colorectal cancer comprising (a) obtaining a biological sample from a subject; (b) assessing the biological sample for (i) FJX1 activity or (ii) the level of a FJX1 protein or nucleic acid; (c) comparing the level of FJX1 observed in step (b) with a comparable sample from a normal subject; and (d) diagnosing the presence or absence of colorectal cancer based on step (c). The sample may be a tissue sample, such as a biopsy, or a biological fluid sample, such as lymph, plasma, urine, feces or blood. Step (b) may comprise assessing the level of a FJX1 protein, such as by immunologic detection (e.g., immunofluorescence, ELISA, RIA, or Western blot), or assessing the level of a FJX1 nucleic acid (e.g., an mRNA, or genomic DNA), including determining loss of heterozygosity. PCR is specifically contemplated as a methodology for examining the nucleic acid. Step (b) may also comprises assessing the FJX1 Notch signaling activity. Step (c) may comprise referencing a previously determined normal level, or may comprise obtaining the comparable sample and assessing the comparable sample for (i) FJX1 activity or (ii) the level of a FJX1 protein or nucleic acid.

In another embodiment, there is provided a method of inhibiting a colorectal (CR) cancer cell comprising contacting the CR cancer cell with an agent that reduces FJX1 function. The CR cancer cell may be a primary cancer cell, a metastatic cancer cell, a recurrent cancer cell or a multidrug resistant cancer cell. The agent may comprise an anti-FJX1 antibody, a FJX1 inhibitory nucleic acid, such as an siRNA. The agent may also comprise a peptide or polypeptide that binds to FJX1, or an expression construct that encodes a proteinanceous agent. The method may further comprise contacting the CR cancer cell with a second anticancer therapy, such as gene therapy, hormonal therapy, chemotherapy, radiation therapy, immunotherapy, or toxin therapy. The second anticancer therapy may be provided before or at the same time as the agent, or be provided after the agent. The CR cancer cell may be a human CR cancer cell, such one located in a human subject and the human CR cancer cell is part of a tumor. The agent may be delivered intratumorally, into the tumor vasculature, into a resected tumor bed, local to the tumor or regional to the tumor. The method may further comprise surgery.

In still another embodiment, there is provided a method of screening candidate substance for anti-cancer activity comprising (a) providing a cell that expresses FJX1; (b) contacting the cell with a candidate substance; and (c) assessing the effect of the candidate substance of FJX1 expression or function, wherein a candidate substance that inhibits FJX1 expression and/or function is identified as having anti-cancer activity. The cell may be a cancer cell, for example, one that overexpresses FJX1 as compared to a non-cancer cell. The candidate substance may be a peptide, a polypeptide, a nucleic acid or a small molecule pharmaceutical. Assessing expression may comprise Northern blot, RT-PCR, ELISA, or RIA. Assessing function may comprise assessing FJX1 Notch signaling, such as by assessing the expression of FJX1 Notch-regulated genes. The cell may be engineered to express a marker protein under the control of the native FJX1 promoter. The method may further comprise contacting the cell with at least a second anti-cancer therapy, such as gene therapy, hormonal therapy, chemotherapy, radiation therapy, immunotherapy, or toxin therapy.

In still a further embodiment, there is provided a method of predicting outcome of colorectal cancer comprising (a) obtaining a biological sample from a subject having colorectal cancer; (b) assessing said biological sample for (i) FXJ1 activity or (ii) the level of a FJX1 protein or nucleic acid; (c) comparing the activity or level of FJX1 observed in step (b) with a known FJX1 activity or level; and (d) correlating a relative increase in activity or level of FJX1 as compared to the known activity or level with poor outcome of colorectal cancer in said subject. The relative increase may be compared to a subject that has colorectal cancer that has progressed, or a subject that has colorectal cancer that has not progressed. Th relative increase may also be with respect to a sample taken at an earlier time from said subject, and may reflect progression (increased), remission (decreased) or therapeutic efficacy (decreased) of an administered treatment. The sample may be a tissue sample, such as a biopsy. The sample may be a biological fluid sample, such as lymph, plasma, urine, feces or blood. Step (b) may comprise assessing the level of a FXJ1 protein, such as by immunologic detection, e.g., immunofluorescence, ELISA, RIA, or Western blot. Step (b) may comprise assessing the level of a FXJ1 nucleic acid, such as an mRNA or a genomic DNA (e.g., assessing loss of heterozygosity). Assessing may comprise PCR. Step (b) may also comprise assessing the FXJ1 Notch signaling activity.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIG. 5A) Effect of modulation of claudin-1 on ZEB-1 and E-cadherin expression in SW480, SW480claudin-1, SW620 and SW620$^{siRNA}$ cells. Cells were detached using EDTA and plated on polyhema coated plates and were collected after 0, 3, 8 and 24 hrs. Equal amounts of total protein (25 µg) was loaded was electrophoresed onto a 8% SDS-PAGE and immunoblotted with ZEB-1 antibody. (FIG. 5B) Equal amounts of total protein (25 µg) from various tissue extracts from five different patients under study were electrophoresed and immunoblotted with claudin-1, ZEB-1 and E-cadherin RNA levels were examined by RT-PCR in SW480, SW480$^{claudin-1}$, Sw620 and Sw620$^{siRNA}$ cells.

(FIG. 10A) Scheme for serially enriching invasive MC38 cells. Briefly, 2.5×10$^5$ cells were plated in a Transwell invasive Chamber coated by Matrigel (2.5 mg/ml). Invasive MC-38 cells were collected from the bottom side of chamber after 24 hours. After 6 passages, invasive cells were enriched (MC38inv). (FIG. 10B) shows quantification of invasion by MC-38inv vs. parental MC-38 cells.

(FIG. 12A) Lungs from mice injected with MC-38 (FIG. 12B) Lungs from mice injected MC-38Lu showing numerous metastatic lesions (arrows) (FIG. 12C) Graphic representation of lung weights in MC-38 and MC-38Lu injected mice at time of autopsy, reflecting relative tumor burden.

(FIG. 18A) Notch activity in HEK293 cells following treatment with NICD, NICD+200 nM DAPT, LNG (negative control), LNG+200 nM DAPT and 200 nM DAPT. (FIG. 18B) Notch promoter activity in HEK293 cells following treatment with dnMAM, NICD, NICD+dnMAM, LNG and LNG+dnMAM.

(FIG. 21A) FJX1 immunoblots of SW480 human colon cancer protein lysates blocked with 3 μg/μl peptide, as indicated in the figure. (FIG. 21B) FJX protein in metastatic (SW480$^{Claudin\ 1}$) and non-metastatic (SW620$^{Claudin1KD}$) derivatives of SW480 and SW620. (FIG. 21C) FJX protein in the mouse colon cancer cell line, MC-38, is upregulated in the highly metastatic derivative line, MC-38Lu.

DETAILED DESCRIPTION OF THE PREFERRED EMBODIMENTS

I. The Present Invention

Figure 1:
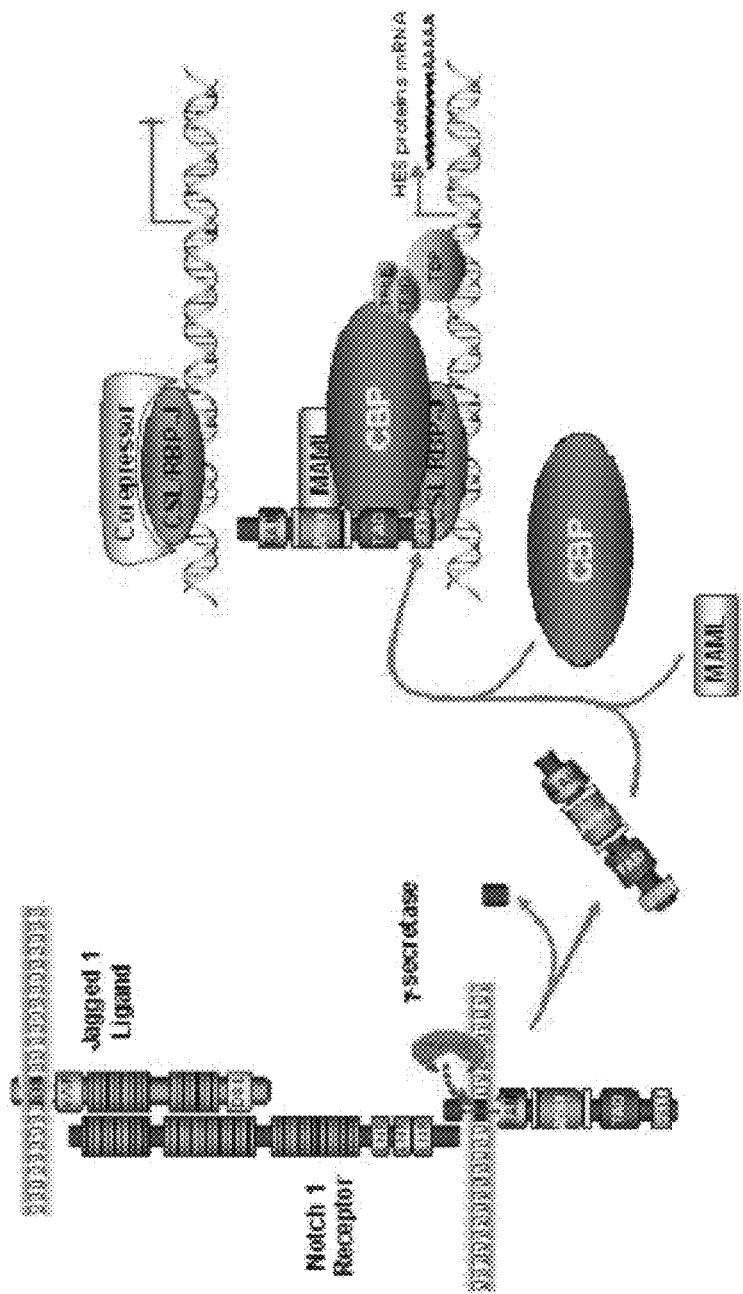
FIG. 1—Notch Signaling Pathway. Both the Notch1 receptor and it's ligand(s), Jagged (and Delta) are plasma membrane associated proteins mediating cell-cell interaction in development and organogenesis. Activity in the Notch signalling pathway is regulated by series of proteases, among them TACE and γ-secretase. Upon release from the Notch receptor by γ-secretase, NCID translocates to the nucleus where it directs transcription of HES and other products.

Here, the inventors describe evidence of increased expression of the Notch-related four jointed box 1 (fjx1) gene in human colorectal carcinoma, the down-regulation of expression of this gene by expression of Smad4 in Smad4-deficient cultured colon cancer cells and by inhibition of COX-2 activity by celecoxib (Celebrex®) in human rectal tumor samples (comparing pre- and post-celecoxib treatment biopsies). Thus, FJX1 provides both a diagnostic/prognostic marker for colorectal cancer as well as a putative therapeutic target, the inhibition of which could provide treatment for various types of FJX1-involved cancers.

II. FJX1

The fjx1 gene is the mammalian homologue of the Drosophila gene four-jointed (fj) (Rock et al., 2005a). The four-jointed gene has been found to be a downstream target of the Notch signaling pathway in leg segmentation and planar cell polarity processes during eye development in Drosophila. Little is known of the function of the fj gene, but mutations lead to loss of an intermediate joint in the Drosophila leg and a planar cell polarity defect in the eye with associated wrong orientation and chirality of ommatidia (polarized optic cuticle structures) (Zeidler et al., 1999b). In Drosophila, fj expression in response to Notch signaling provides a positive feedback loop for the expression of Notch ligands Delta and Serrate (mammalian homolog Jagged). Four-jointed also interacts with the Drosophila genes abelson, enabled and dachs which are known to play significant roles in microfilament dynamics, thus linking fj signaling to the actin cytoskeleton (Buckles et al., 2001). In addition to Notch, activation of JAK/STAT in Drosophila also induced expression of fj, while Wingless (Wg) signaling inhibited its expression (Zeidler et al., 1999b).

FJX1, shown in SEQ ID NO: 1, is a secretory protein in both vertebrates and Drosophila (FJ), and is highly conserved from Drosophila to Homo sapiens. In the mouse, fjx1 is highly expressed in the developing brain, and all developing neural structures. It is also expressed in epithelial cells of many structures that develop via epithelial-mesenchymal interactions, such as the tooth bud, whisker follicles, thymus, submandibular glands, pancreas and the gut endoderm (Rock et al., 2005a; Rock et al., 2005b). To date, there are only four articles on FJX1 identified in a PubMed search, and its function in mammalian organisms remains unknown. However, the regulation and function of the Drosophila ortholog four-jointed (fj) may be relevant to its regulation and function in higher organisms and in carcinogenesis. FJX1 may function as a ligand for a receptor as yet to be identified because Rock et al. (2005a) identified localization of recombinant FJX1-alkaline phosphatase fusion protein in brain tissue adjacent to the location of fjx1 mRNA expression and in lung and kidney there was overlapping localization of binding and expression. The evidence that fjx1 is a Notch target gene is based on the homology of mouse fjx1 with Drosophila fj, and on the findings by Rock et al. (2005a) that co-transfection of Notch 1-3, but not Notch4, with the fjx1 promoter-luciferase reporter gene resulted in robust transactivation of the reporter. Transactivation of the reporter was largely lost after deletion of a RBP-J binding site in the minimal proximal fjx1 promoter-reporter construct. However, the same group found no change in fjx1 expression in Notch1 null mice and only occasionally decreased expression in delta-like 1 knockout mice. They stated that early lethality in both knockout genotypes precluded analysis of later embryonic stages where higher fjx1 expression levels could be detected. Thus, clear-cut in vivo evidence of Notch-dependent fjx1 expression currently is lacking. As stated above, little is known of the role of FJX1 in vertebrate biology.

A. Variants of FJX1

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent or improved molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |

TABLE 1-continued

| Amino Acids | | | Codons |
|---|---|---|---|
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making substitutional variants, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within +2 is preferred, those which are within ±1 are particularly preferred, and those within +0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within +2 is preferred, those that are within +1 are particularly preferred, and those within 10.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of FJX1, but with altered and even improved characteristics.

B. Domain Switching

Domain switching involves the generation of chimeric molecules using different but, in this case, related polypeptides. By comparing the FJX1 sequence with related proteins, one can make predictions as to the functionally significant regions of these molecules. It is possible, then, to switch related domains of these molecules in an effort to determine the criticality of these regions to FJX1 function. These molecules may have additional value in that these "chimeras" can be distinguished from natural molecules, while possibly providing the same function. Of particular use in this regard are non-human homologs from mouse, chicken, zebrafish and *Drosophila*.

C. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It will be desirable to purify FJX1 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fructose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Synthetic Peptides

The present invention also describes smaller FJX1-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antigen Compositions

The present invention also provides for the use of FJX1 proteins or peptides as antigens for the immunization of animals relating to the production of antibodies. It is envisioned that either FJX1, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding FJX1 or portions thereof. The gene for the human FJX1 molecule has been identified and previously described, as have the corresponding genes from *Drosophila*, mouse, chicken, zebrafish, and xiphosphorous. The present invention is not limited in scope to these genes, however, as one of ordinary skill in the could readily identify related homologs in various other species (e.g., rat, rabbit, dog. monkey, gibbon, chimp, ape, baboon, cow, pig, horse, sheep, cat).

In addition, it should be clear that the present invention is not limited to the specific nucleic acids disclosed herein. As discussed below, a "FJX1 gene" may contain a variety of different bases and yet still produce a corresponding polypeptide that is functionally indistinguishable from, and in some cases structurally identical to, the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of FJX 1.

A. Nucleic Acids Encoding FJX1

Nucleic acids according to the present invention may encode an entire FJX1 protein, a particular structural domain of FJX1, or any other fragment of the FJX1 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given FJX1 from a given species may be represented by natural variants that have slightly different nucleic acid sequences but, nonetheless, encode the same protein (see Table 1, above).

As used in this application, the term "a nucleic acid encoding a FJX1" refers to a nucleic acid molecule that has been isolated free of total cellular nucleic acid. In certain embodiments, the invention concerns a nucleic acid sequence essentially as set forth in SEQ ID NO:2, the human sequence. The term "as set forth in SEQ ID NO:2" means that the nucleic acid sequence substantially corresponds to a portion of SEQ ID NO:2. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:2. Sequences that are essentially the same as those set forth in SEQ ID NO:2 also may be functionally defined as sequences that are capable of hybridizing to a nucleic acid segment containing the complement of SEQ ID NO:2 under standard conditions.

The DNA segments of the present invention include those encoding biologically functional equivalent FJX1 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NO:2. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 under relatively stringent conditions such as those described herein. Such sequences may encode the entire FJX1 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to FJX1 or, more particularly, homologs of FJX1 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as $E.\ coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.\ coli$ cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of FJX1 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments, expression vectors are employed to express the FJX1 polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(i) Regulatory Elements

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example is the native FJX1 promoter, set forth in SEQ ID NO: 3. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996). Tumor specific promoters also will find use in the present invention. Some such promoters are set forth in Tables 4 and 5.

TABLE 4

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas cells | Type II pneumocytes; Clara |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |

TABLE 4-continued

Candidate Tissue-Specific Promoters for Cancer Gene Therapy

| Tissue-specific promoter | Cancers in which promoter is active | Normal cells in which promoter is active |
|---|---|---|
| Keratin 14 | Presumably many squamous cell carcinomas (e.g., Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 5

Candidate Promoters for Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP7S expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

(ii) IRES

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

(iii) Multi-Purpose Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

(iv) Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, herein incorporated by reference.)

(v) Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

(vi) Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

(vii) Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

(viii) Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations. Antibodies are and their uses are discussed further, below.

III. Generating Antibodies Reactive With FJX1

In another aspect, the present invention contemplates an antibody that is immunoreactive with a FJX1 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

(ix) Viral Vectors

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

Adenoviral Vectors. In particular embodiments, an adenoviral expression vector is contemplated for the delivery of expression constructs. "Adenovirus expression vector" is meant to include those constructs containing adenovirus sequences sufficient to (a) support packaging of the construct and (b) to ultimately express a tissue or cell-specific construct that has been cloned therein.

Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a $\psi$ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, and function as origins of replication and are necessary for viral DNA replication. The v sequence is required for the packaging of the adenoviral genome.

A common approach for generating an adenoviruses for use as a gene transfer vector is the deletion of the E1 gene (E1$^-$), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; and 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient. Armentano et al. (1990), describe the preparation of a replication-defective adenovirus vector, claimed to eliminate the potential for the inadvertent generation of a replication-competent adenovirus (U.S. Pat. No. 5,824,544, specifically incorporated herein by reference). The replication-defective adenovirus method comprises a deleted E1 region and a relocated protein 1× gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different known serotypes and/or sub-groups A-F. Adenovirus type 5 of subgroup C is the preferred starting material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. Nos. 5,670,488; 5,932,210; and 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaagen, 1998), coronary diseases (Feldman et al., 1996), muscular diseases (Petrof, 1998), gastrointestinal diseases (Wu, 1998) and various cancers such as colorectal (Fujiwara and Tanaka, 1998; Dorai et al., 1999), pancreatic, bladder (Irie et al., 1999), head and neck (Blackwell et al., 1999), breast (Stewart et al., 1999), lung (Batra et al., 1999) and ovarian (Vanderkwaak et al., 1999).

Retroviral Vectors. In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. Nos. 5,858,744; and 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. Nos. 5,955,331; and 5,888,502, each specifically incorporated herein by reference). Nolan et al. describe the production of stable high titre, helper-free retrovirus comprising a heterologous gene (U.S. Pat. No. 5,830,725, specifically incorporated herein by reference). Methods for constructing packaging cell lines useful for the generation of helper-free recombinant retroviruses with amphoteric or electrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector-mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV), simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999; White et al., 1999; Case et al., 1999). For example, HIV-based vectors have been used to infect non-dividing cells such as neurons (Miyatake et al., 1999), islets (Leibowitz et al., 1999) and muscle cells (Johnston et al., 1999). The therapeutic delivery of genes via retroviruses are currently being assessed for the treatment of various disorders such as inflammatory disease (Moldawer et al., 1999), AIDS (Amado et al., 1999; Engel and Kohn, 1999), cancer (Clay et al., 1999), cerebrovascular disease (Weihl et al., 1999) and hemophilia (Kay, 1998).

Herpesviral Vectors. Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Gamido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. Nos. 5,879,934; and 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B-cell malignancies (Suzuki et al., 1998), ovarian cancer (Wang et al., 1998) and Duchenne muscular dystrophy (Huard et al., 1997).

Adeno-Associated Viral Vectors. Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

Lentiviral Vectors. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

Lentiviral vectors are known in the art, see Naldini et al., (1996); Zufferey et al., (1997); U.S. Pat. Nos. 6,013,516; and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene, such as the STAT-1α gene in this invention, into that packaging cell yields a producer cell which releases infectious viral particles carrying the foreign gene of interest. The env preferably is an amphotropic envelope protein which allows transduction of cells of human and other species.

One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

The heterologous or foreign nucleic acid sequence, such as the STAT-1α encoding polynucleotide sequence herein, is linked operably to a regulatory nucleic acid sequence. Preferably, the heterologous sequence is linked to a promoter, resulting in a chimeric gene. The heterologous nucleic acid sequence may also be under control of either the viral LTR promoter-enhancer signals or of an internal promoter, and retained signals within the retroviral LTR can still bring about efficient expression of the transgene. Marker genes may be utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate, etc., and cell surface markers.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Lentiviral transfer vectors Naldini et al. (1996), have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector showed no decrease in the average level of transgene expression and no sign of tissue pathology or immune reaction (Blomer et al., 1997). Thus, in the present invention, one may graft or transplant cells infected with the recombinant lentivirus ex vivo, or infect cells in vivo.

Other Viral Vectors. The development and utility of viral vectors for gene delivery is constantly improving and evolving. Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference).

In other embodiments, sindbis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879, specifically incorporated herein by reference).

Chimeric Viral Vectors. Chimeric or hybrid viral vectors are being developed for use in therapeutic gene delivery and are contemplated for use in the present invention. Chimeric poxviral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are the viral sequences from which the rep and cap polypeptide encoding sequences are deleted. More specifically, the AAV sequences employed are the cis-acting 5' and 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease.

(x) Non-Viral Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

Injection. In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

Electroporation. In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazzerri, 1995), sorghum (Battraw et al., 1991), maize (Bhattacharjee et al., 1997), wheat (He et al., 1994) and tomato (Tsukada, 1989).

Calcium Phosphate. In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

DEAE-Dextran: In another embodiment, a nucleic acid is delivered into a cell using DEAE-dextran followed by polyethylene glycol. In this manner, reporter plasmids were introduced into mouse myeloma and erythroleukemia cells (Gopal, 1985).

Sonication Loading. Additional embodiments of the present invention include the introduction of a nucleic acid by direct sonic loading. LTK$^-$ fibroblasts have been transfected with the thymidine kinase gene by sonication loading (Fechheimer et al., 1987).

Liposome-Mediated Transfection. In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Receptor Mediated Transfection: Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

G. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

H. Cell Propagation

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to FJX1-related antigen epitopes. Additionally, it is proposed that monoclonal antibodies specific to the particular FJX1 of different species may be utilized in other useful applications In general, both polyclonal and monoclonal antibodies against FJX1 may be used in a variety of embodiments. For example, they may be employed in antibody cloning protocols to obtain cDNAs or genes encoding other FJX1. They may also be used in inhibition studies to analyze the effects of FJX1 related peptides in cells or animals. Anti-FJX1 antibodies will also be useful in immunolocalization studies to analyze the distribution of FJX1 during various cellular events, for example, to determine the cellular or tissue-specific distribution of FJX1 polypeptides under different points in the cell cycle. A particularly useful application of such antibodies is in purifying native or recombinant FJX1, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified FJX1 protein, polypeptide or peptide or cell expressing high levels of FJX1. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IV. Diagnosing Cancers Involving FJX1

FJX1 and the corresponding gene may be employed as a diagnostic or prognostic target for cancer. More specifically, the overexpression of FJX1, as compared to levels observed in corresponding normal tissue types, may cause or promote cancer development, cause or promote tumor progression at a primary site, and/or cause or promote metastasis. Other phenomena associated with malignancy that may be affected by FJX1 expression include angiogenesis and tissue invasion.

A. Genetic Diagnosis

One embodiment of the instant invention comprises a method for detecting variation in the expression of FJX1. This may comprises determining that level of FJX1 or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of gliomas.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have FJX1-related pathologies. In this way, it is possible to correlate the amount or kind of FJX1 detected with various clinical states.

Various types of defects have been identified by the present inventors. Thus, "alterations" should be read as including deletions, insertions, point mutations and duplications. The only requirement is that the mutation result in a net gain of function. Another type of gane of function mutation is one that does not alter the FJX1 protein, but instead causes its overexpression. This is typically measured by assessing transcript (mRNA) levels in a quantitative or semi-quantitative fashion.

It is contemplated that various mutations in the FJX1 gene may be identified in accordance with the present invention. A variety of different assays are contemplated in this regard, including but not limited to, Northern blot, RT-PCR, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process. In particular embodiments, the probes or primers are labeled with radioactive species ($^{32}P$, $^{14}C$, $^{35}S$, $^{3}H$, or other label), with a fluorophore (rhodamine, fluorescein) or a chemiluminescent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single-stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the FJX1 gene that may then be analyzed by direct sequencing.

(vi) Kit Components

All the essential materials and reagents required for detecting and sequencing FJX1 and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the FJX1 content of healthy and diseased tissues, through techniques such as immunohistochemistry, ELISAs and Western blotting. This may provide a screen for the presence or absence of malignancy or as a predictor of future cancer.

The use of antibodies of the present invention, in an ELISA assay is contemplated. For example, anti-FJX1 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for FJX1 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. Methods of Therapy

The present invention also involves, in another embodiment, the treatment of cancer. The types of cancer that may be treated, according to the present invention, is limited only by the involvement of FJX1. Thus, it is contemplated that a wide variety of tumors may be treated using FJX1 therapy, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Nucleic Acid-Based Therapies

One of the therapeutic embodiments contemplated by the present inventors is the intervention, at the molecular level, in the events involved in tumorigenesis. Specifically, the present inventors intend to provide, to a cancer cell, a nucleic acid that interferes with the expression of FJX1 in that cell. Because the sequence homology between human FJX1 and other homologs, any of these nucleic acids could be used in human therapy. The interfering nucleic acid could be an a single-chain antibody construct, an antisense construct, a ribozyme or a siRNA. These nucleic acids may be delivered in a form that directly interferes with the expression of FJX1, or they may be provided in expression constructs that utilize enzymes within the cell to express the interfering nucleic acids. Thus, the lengthy discussion of expression vectors and the genetic elements employed therein is incorporated into this section by reference. Particular expression vectors are viral vectors such as adenovirus, adeno-associated virus, herpesvirus, vaccinia virus and retrovirus. Also contemplated are liposomally-encapsulated expression vectors.

Those of skill in the art are well aware of how to apply nucleic acid delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way FJX1 may be utilized according to the present invention.

B. Protein Therapy

Another therapy approach is the provision, to a subject, of FJX1 fragments, synthetic peptide, mimetic or other analogs thereof that can interact with one or more FJX1 binding partner, but do so such that the function of FJX1 is not mimicked. Formulations would be selected based on the route of administration and purpose including, but not limited to, liposomal formulations and classic pharmaceutical preparations. FJX1 antibodies also may be applied in this fashion.

C. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with other therapies. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that FJX1 therapy, as discussed above, could be used similarly in conjunction with chemo- or radiotherapeutic intervention. It also may prove effective to combine FJX1 therapy with immunotherapy.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with an FJX1-targeted agent and at least one other agent. These compositions would be provided in a combined amount effective to kill or inhibit proliferation of the cell. This process may involve contacting the cells with the FJX1 agent and the other agent or factor at the same time. This may be achieved by contacting the cell with a single composition or pharmacological formulation that includes both agents, or by contacting the cell with two distinct compositions or formulations, at the same time, wherein one composition includes the FJX1 agent and the other includes the other agent.

Alternatively, the gene therapy treatment may precede or follow the other agent treatment by intervals ranging from minutes to weeks. In embodiments where the agents are applied separately to the cell, one would generally ensure that a significant period of time did not expire between the time of each delivery, such that the two agents would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the FJX1 agent or the other agent will be desired. Various combinations may be employed, where the FJX1 agent is "A" and the other agent is "B," as exemplified below:

| A/B/A | B/A/B | B/B/A | A/A/B |
|-------|-------|-------|-------|
| B/A/A | A/B/B | B/B/B/A | B/B/A/B |
| A/A/B | A/B/A/B | A/B/B/A | B/B/A/A |
| B/A/B/A | B/A/A/B | B/B/B/A | A/A/A/B |
| B/A/A/A | A/B/A/A | A/A/B/A | A/B/B/B |
| B/A/B/B | B/B/A/B | | |

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a FJX 1 targeted agent is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with an FJX1 targeted agent, as described above.

Agents that directly cross-link nucleic acids, specifically DNA, are envisaged to facilitate DNA damage leading to a synergistic, antineoplastic combination with FJX1. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of the FJX1 agent to patients with cancer will be a very efficient method for treating the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining FJX1 therapies with chemo- and radiotherapies, it also is contemplated that combination with other gene therapies will be advantageous. For example, targeting of FJX1 and p53 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Kits

According to the present invention, there are provided kits for detecting fjx1 mutations, fjx1 transcripts and FJX1 proteins. The kit of the present invention can be prepared by known materials and techniques which are conventionally used in the art. Generally, kits comprises separate vials or containers for the various reagents, such as probes, primers, enzymes, antibodies, etc. The reagents are also generally prepared in a form suitable for preservation by dissolving it in a suitable solvent. Examples of a suitable solvent include water, ethanol, various buffer solutions, and the like. The various vials or containers are often held in blow-molded or injection-molded plastics.

VII. Transgenics

In one embodiment of the invention, transgenic animals are produced which contain a functional transgene encoding a functional human FJX1 polypeptide or variants thereof. Transgenic animals expressing FJX1 transgenes, recombinant cell lines derived from such animals and transgenic embryos may be useful in methods for screening for and identifying agents that induce or repress function of FJX1. Transgenic animals overxpressing homologous or heterologous FJX1 can be used as models for studying cancers, such as colorectal cancers. The promoter controlling the transgene may be one that is capable of tissue specific or inducible expression. Within a particularly preferred embodiment, transgenic mice are generated which overexpress FJX1 or express a mutant form of the polypeptide.

In one embodiment of the invention, a fjx1 transgene is introduced into a non-human host to produce a transgenic animal expressing a human or murine FJX1 gene. The transgenic animal is produced by the integration of the transgene into the genome in a manner that permits the expression of the transgene. Methods for producing transgenic animals are generally described by Wagner and Hoppe (U.S. Pat. No. 4,873,191; incorporated herein by reference), Brinster et al. (1985; incorporated herein by reference) and in Hogan, "Manipulating the Mouse Embryo; A Laboratory Manual" (1994; incorporated herein by reference).

It may be desirable to replace the endogenous FJX1 by homologous recombination between the transgene and the endogenous gene so as to measure the effects of only the transgene's expression. Typically, a fjx1 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Alternatively, the endogenous gene may be eliminated by deletion as in the preparation of "knock-out" animals, optionally followed by insertion of the FJX1 transgene. the absence of one or both alleles of a FJX1 gene in "knock-out" mice permits the study of the effects that a reduction in or loss of FJX1 protein has on a cell in vivo. Knock-out mice also provide a model for the development of FJX1-related cancers.

As noted above, transgenic animals and cell lines derived from such animals may find use in certain testing experiments. In this regard, transgenic animals and cell lines capable of expressing wild-type or mutant FJX1 may be exposed to test substances. These test substances can be screened for the ability to enhance wild-type FJX1 expression and or function or impair the expression or function of mutant FJX1.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Through a combined approach of analysis of fresh human colorectal cancer specimens, mechanistic studies in colorectal cancer cell lines, and selected experiments in mouse models of human colorectal cancer, the inventors have sought to extend our understanding of cancer biology. In particular, the prevailing evidence supports the hypothesis that invasive and metastatic behavior in cancer cells is a regulated biological process, and as such, may be susceptible to therapeutic targeting as the underlying mechanisms are better understood. The inventors have obtained a large number of human colorectal cancer specimens and analyze global changes in gene expression among these samples using the genome wide Affymetrix Oligonucleotide Microarray.

Figure 2:
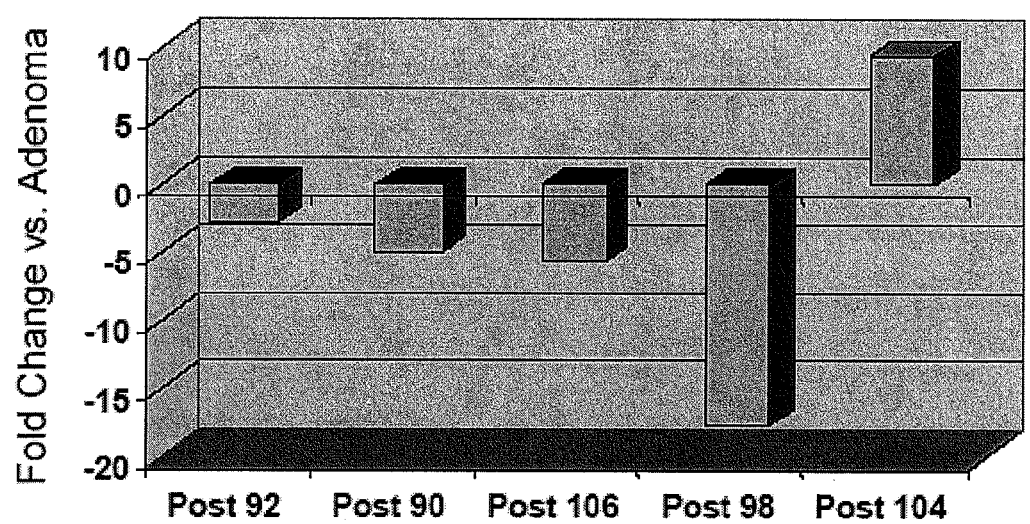
FIG. 2—Validation of Celebrex-induced changes in FJX1 gene expression by qRT-PCR. Real-time PCR data shows FJX1 levels down-regulated in tissue biopsies from 4/5 randomly selected rectal cancer patients after treatment with Celebrex. FJX1 expression is compared to pre-treatment expression. RNA was harvested and purified via the RNeasy™ kit (Qiagen). Real-time PCR was performed on the iCycler™ platform (BioRad) after cDNA was plated on a 96-well plate and expression values were normalized to the phosphomannomutase (PMM1) housekeeping gene for the final analysis.

As part of an Institutional Review Board-approved clinical trial to test the effect of celecoxib on rectal cancer, the inventors have analyzed rectal tumors from 16 patients with rectal cancer via Affymetrix GeneChip microarray (Affymetrix U133 Plus 2.0 gene chip microarray platform). The patients underwent endoscopic pinch biopsies both before and after one week of celecoxib treatment (400 mg twice per day) and before any other treatment. The effect of celecoxib on COX-2 activity was confirmed by demonstrating a significant decrease in the urinary metabolite of PGE2, PGE-M, among these patients when comparing pre-versus post-celecoxib treatment as reported in Johnson et al. (2006). The tumor samples submitted for microarray analysis included: 3-stage 1 cancers, 7-stage 2 cancers, and 6-stage 3 cancers. The inventors' initial evaluation uncovered 13 genes whose expression was significantly different in comparing pre-treated to those after celecoxib treatment (Table 6). Quantitative real-time RT-PCR validation for FJX1 expression was carried out in a random selection of 5 of the 16 rectal cancer patients, and FJX1 mRNA was verified down-regulated in four of the five rectal cancers after Celecoxib treatment (FIG. 2). Phosphomannomutase (PMM1), a housekeeping gene of constant expression is used as an internal control on all qRT-PCR experiments (Rubie et al., 2005).

The identification of the Notch pathway gene, FJX1, in the above study, along with recent evidence of Notch involvement in colorectal epithelial differentiation and carcinogenesis led us to examine this pathway more closely in colorectal cancer specimens. In addition to the celecoxib study mentioned above, the inventors currently have full genomic expression data (across 54674 probe set IDs) from Affymetrix GeneChip microarray for 38 patients with colon cancer. This evaluation includes: 5 stage 0 patients, 9 stage 2 patients, 9 stage 3 patients, and 15 stage 4 patients. Given the observed increase in the Notch-related FJX1 in colorectal carcinomas, we then asked whether there was other evidence of increased Notch signaling in colorectal cancers assessed in our microarray experiment. The inventors have identified preliminary evidence of the upregulation of multiple Notch signaling pathway genes among the cancers as compared with adenomas that were analyzed in this study (see Table 7). Predictably, COX2 expression is greater in cancers as compared with adenomas. While these data are highly suggestive and are exciting, they are not considered to be definitive evidence due to the lack of power because of insufficient numbers of samples. Currently, the inventors have already submitted an additional 15 colorectal cancer samples for microarray analysis, and have collected an additional 63 matched tumor/normal colorectal cancer samples that they plan to submit for microarray analysis. Over a period of the next 3-5 years, the follow up data on this patient cohort will also mature with sufficient numbers of recurrences to enable linkage of the microarray findings with disease-free and overall survival.

Figure 3:
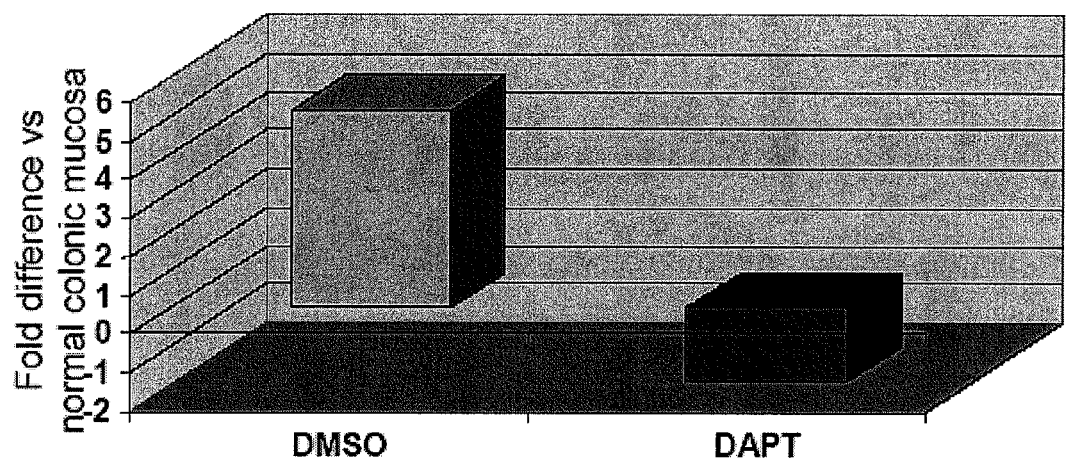
FIG. 3—Decreased FJX1 expression following inhibition of γ-secretase (DAPT) in SW480 colon cancer cells. Cells were grown to 70-80% confluence using complete RPMI and then treated with 200 nM of DAPT or vehicle. The RNA was harvested 16 hrs later using an RNeasy™ kit (Qiagen). qRT-PCR was performed as outlined in the text. Gene expression values were normalized to a housekeeping gene (PMM1) for the final analysis. The values are expressed as fold-change in comparison to normal colonic mucosal levels.

The inventors then assessed expression of FJX1 mRNA in several human colon cancer cell lines and found that in comparison to levels in colorectal adenomas we detected abundant expression of FJX1 in both SW480 and SW620 cells, and less abundant expression in HT29 celsas determined by quantitative real-time RT-PCR (data not shown). Since four-jointed in *Drosophila* is regulated by Notch signaling, and mouse fjx1 expression appears to be a target of Notch regulation, the inventors predicted that inhibition of Notch signaling would inhibit FJX1 expression in colon cancer cells. A reliable pharmacological method of inhibiting Notch signaling is to block release of the Notch intracellular domain through inhibition of γ-secretase activity (van Es et al., 2005). Therefore, the inventors used a selective inhibitor of γ-secretase, DAPT, or vehicle (DMSO) to treat SW480 and SW620 cells for 16 hrs and determined the effect on levels of FJX1. DAPT reduced the levels of FJX1 mRNA in both SW480 (FIG. 3) and SW620 cells (not shown). While these data demonstrate that FJX1 expression levels are sensitive to DAPT, the inventors cannot rule out that other proteins sensitive to DAPT (such as E-cadherin; Kopan and Ilagan, 2004) may also contribute to the change in FJX1 expression.

Figure 4:
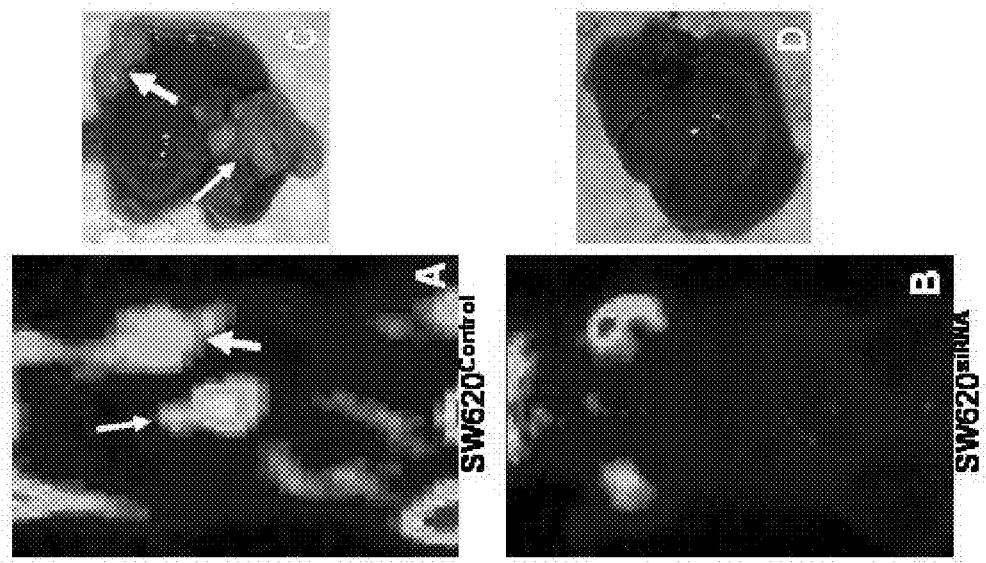
FIGS. 4A-D—SW260 parental cells and cells expressing either SW260$^{control}$ or three individual SW260$^{siRNA}$ clones in nude mice. 5×10$^6$ cells were injected into the spleen, followed by splenectomy after 5 min. Metastatic tumors were detected in the livers of nude mice seven weeks after innoculation by microPET (FIGS. 4A and 4C) and after necroscopy (FIGS. 4B and 4D). MicoPET imaging was used to screen for non-palpable lesions in the liver, using 100-150 µCi for $^{18}$F-deoxyglucose ($^{18}$FDG) to detect metabolically active foci in the abdomen. The arrows point to the metastatic nodules in the liver. The p value was determined using a 2-sided test of proportions.

The inventors have recently published studies demonstrating that claudin-1 expression is increased in human colon carcinoma and that nuclear claudin-1 localization is a frequent occurrence in metastatic lesions (Dhawan et al., 2005). Genetic manipulation of claudin-1 expression in colon cancer cell lines induces changes in cellular phenotype with structural and functional changes in markers of epithelial to mesenchymal transition (EMT). To determine if claudin-1 protein expression has a causal role in colon tumor progression and invasion, the inventors manipulated the levels of claudin-1 expression in primary (SW480) and metastatic (SW620) colorectal cancer cell lines derived from a single patient (Hewitt et al., 2000). To determine if claudin-1 protein expression has a causal role in colon tumor progression and invasion, we manipulated the levels of claudin-1 expression in SW480 and SW620 cells. Over-expression of claudin-1 in SW480 cells (non-metastatic) increased invasiveness through extracellular matrix on in vitro assays and resulted in hepatic metastases when cells were injected into the spleen of athymic nu/nu mice. In contrast, RNA interference-mediated inhibition of claudin-1 levels in metastatic SW620 cells resulted in opposite effects including a significant decrease in hepatic metastases in xenograft experiments (FIG. 4). The inventors further demonstrated that claudin-1 overexpression was linked to downregulation of E-cadherin expression and β-catenin/Tcf transcriptional activity (Dhawan et al., 2005).

In collaboration with Dr. Punita Dhawan, the inventors have initiated experiments to determine which genes and signaling pathways are involved in claudin-1 mediated regulation of colon tumorigenesis and metastasis on a global level, based upon manipulation of claudin-1 expression in SW480 and SW620 colon cancer cell line. They have performed a global analysis of gene expression changes due to modulation of claudin-1 expression. Analysis using Affymetrix Human Genome 230 2.0 GeneChip containing 30,000 genes was performed at the VICC Microarray Core Facility. Although, a very potent tool for discovery, microarray results may be misleading if sufficient replicates and appropriate controls are not included. In this regard, the inventors have developed a model system where over-expression of claudin-1 in SW480 control cells to achieve levels comparable to SW620 control cells resulted in acquisition of metastasis similar to SW620 cells whereas inhibition of claudin-1 expression in SW620 cells resulted in decreased metastasis. Therefore, they used SW480, SW620, three different clones of SW480claudin-1 and three different clones of SW620siRNA for this analysis. Expression data sets were normalized and subtracted for unreliable features such as apparent artifacts and low signals. Thereafter, analysis was performed to identify genes whose expression levels were increased or decreased in all three clones of SW620siRNA cells compared to SW620 control cells. Similarly analysis was done in SW480claudin-1 and SW480 control cells. Thereafter, the inventors selected the genes, which showed increase in SW620siRNA cells compared to SW620 control cells but decreased in SW480claudin-1 compared to SW480 control cells and vice versa. A total of 148 transcripts were identified which passed above criteria and represented genes of known functions.

Consistent with the experimental results described in Dhawan et al. (2005), E-cadherin was one of the transcripts identified as being significantly downregulated in the presence of abundant claudin 1 expression and increased when claudin 1 expression was silenced. The microarray analysis showed a 10-fold increase in E-cadherin mRNA expression in SW620siRNA cells compared to SW620 control cells. The inventors also noted in the microarray results that a known repressor of E-cadherin, TCF8/ZEB-1/δEF-1, was identified in the final list where its expression was upregulated 20-fold in SW480claudin-1 cells compared to SW480 cells and decreased 3.5-fold in SW620siRNA cells as compared with SW620 cells. The inventors observed no changes in either Snail or Slug expression (two genes known to regulate EMT and E-cadherin expression) in SW620siRNA cells compared to SW620 control cells (not shown) and consistently, neither snail nor slug gene expression was identified as significantly altered in the microarray data.

Figure 5:
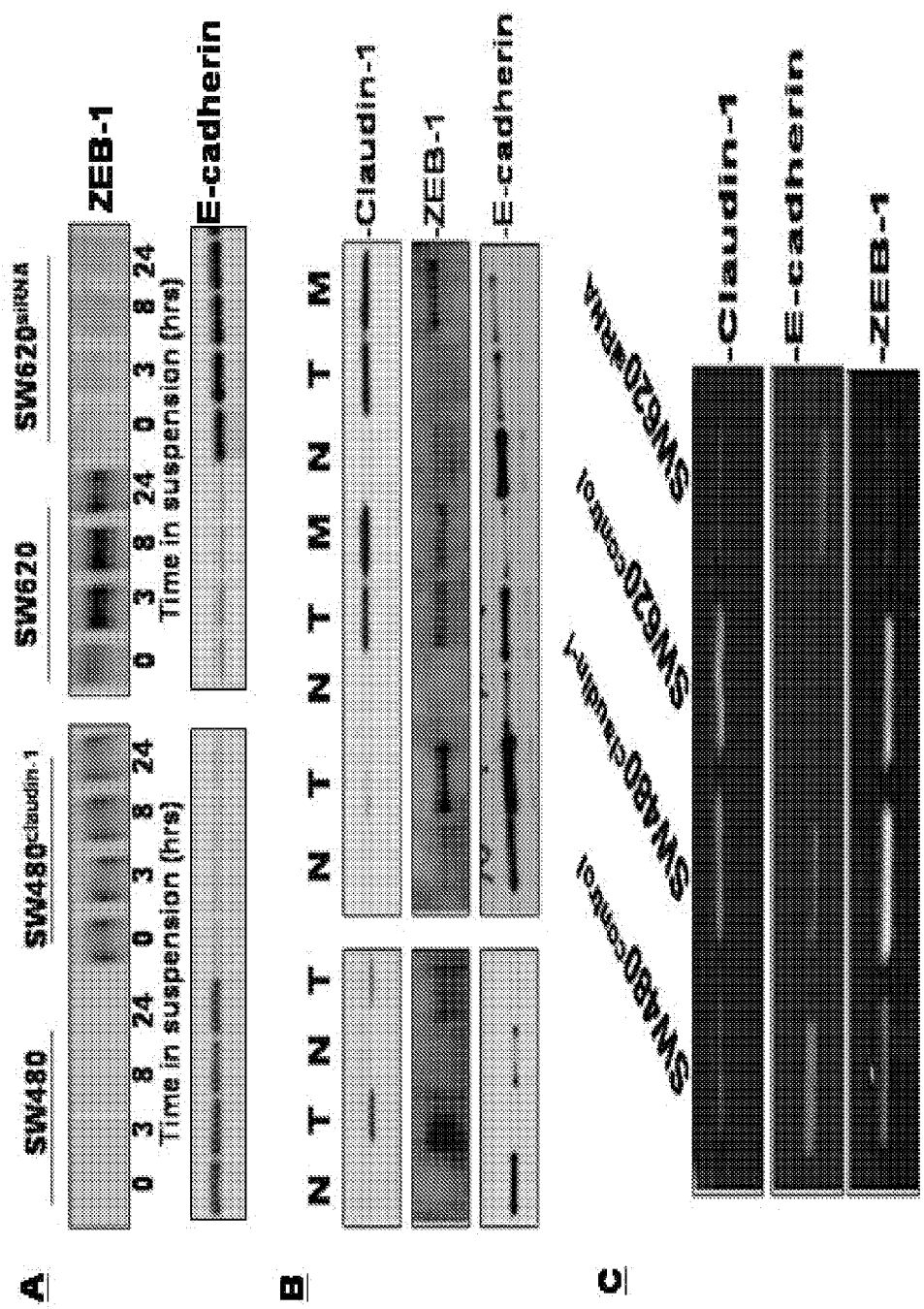
FIGS. 5A-C—Claudin-1 regulates expression of ZEB-1.

The inventors further validated the microarray results with RT-PCR and Western blotting, demonstrating that ZEB-1 RNA and protein expression were indeed upregulated in SW480claudin-1 cells while inhibited in SW620siRNA cells (FIGS. 5A and 5C). Thus, it could be postulated that the effects of modulation of claudin-1 expression on E-cadherin expression is regulated through changes in the expression of ZEB-1. To investigate the significance of this observation in vivo in human colon cancer, the inventors determined the expression of claudin-1, E-cadherin and ZEB-1 in an immunoblot analysis using antigen-specific antibodies and matched samples from normal, colon carcinoma and metastatic human samples. In five out of six samples the inventors observed a direct correlation between expressions of Claudin-1 and ZEB-1, while an inverse correlation with the expression of E-cadherin was observed (FIG. 5B). Interestingly, ZEB-1/TCF8 was found to be significantly upregulated (2.5-fold) while E-cadherin (Cdh1) was significantly decreased in gene expression array of the human colorectal cancers regardless of stage.

Figure 6:
FIG. 6—Effect of ZEB-1 silencing on E-caherin expression in Claudin-1 overexpressing SW480 cells. Immunoblot analysis of ZEB-1 and E-cadherin levels in protein lysates from SW480$^{claudin-1}$ cells 48 hours after transfection with ZEB-1 siRNA.

Such interactions are suggested by the inventors' further exploration of the role of ZEB-1 in tumor cell phenotype. They have found that sustained high level expression of ZEB-1 is required for suppression of E-cadherin expression in claudin-1 overexpressing (metastatic) SW480 cells. When ZEB-1 expression is inhibited by RNA interference, E-cadherin protein expression is increased (FIG. 6).

In the gene expression array experiment on the fresh human colorectal cancer specimens described above, the inventors have assessed expression of potential mediators or indicators of EMT in the human colorectal cancer samples and in addition to the Notch signaling members and targets identified above, they have identified Zeb1/Tcf8 and Zeb2/Sip1 (two known transcriptional repressors of E-cadherin) as being significantly increased across all stages of colorectal cancer as compared with stage 0 adenoma patients. In contrast, Cdh1 (E-cadherin) gene expression is significantly decreased. In addition, we observe increased expression of N cadherin (1.6 increase, p 0.001), MMP9 (3.6 increase, p 0.0001), and vimentin (1.6 increase, p. 1.3×10-5), all consistent with an EMT-associated gene expression profile.

Figure 7:
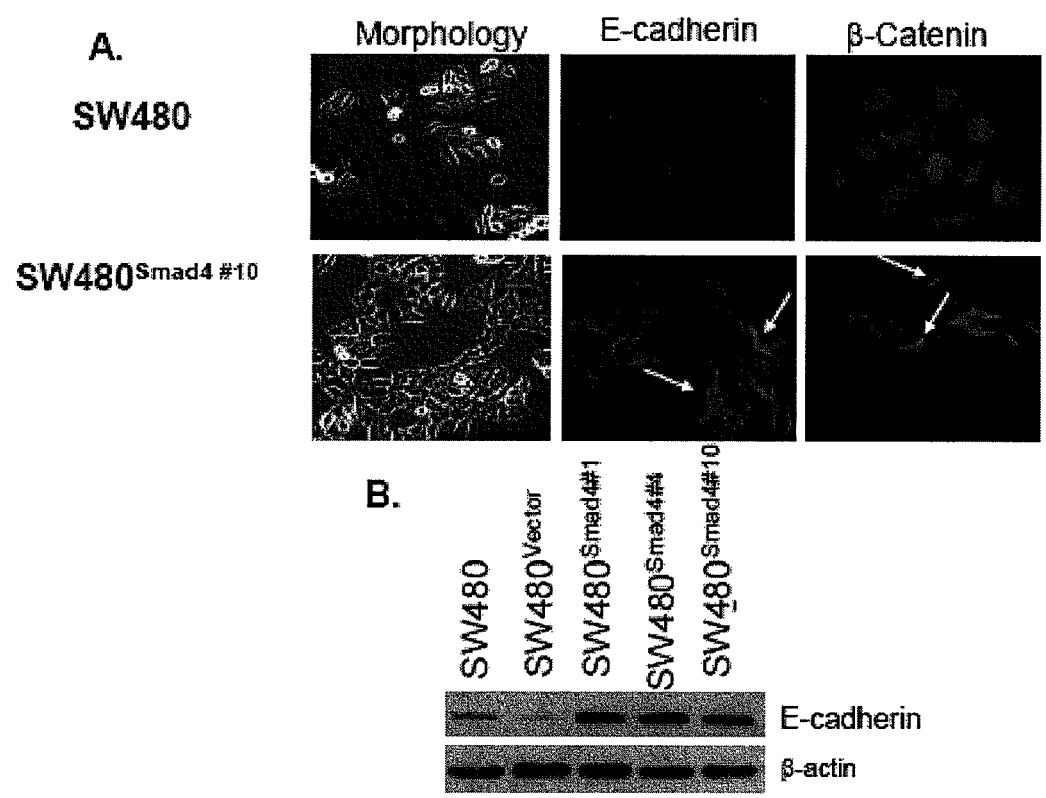
FIGS. 7A-B—Smad4 re-expression results in EMT in SW480 cells. Indicated by (FIG. 7A) morphology, increased expression of E-cadherin and re-distribution of membrane β-catenin by immunofluorescence and by (FIG. 7B) immunoblotting for E-cadherin.

During the course of their examination of the role of claudin-1 in EMT and metastasis, the inventors noted an inverse correlation of claudin-1 and Smad4 expression amongst several colon cancer cell lines. For example, Smad4-null lines SW480, SW620 and HT29 all expressed abundant levels of claudin-1, whereas the Smad4 expressing lines HCT116, HCT15, the immortalized rat small intestinal RIE cells and the immortalized mouse colonocyte (YAMC) line did not express detectable levels of claudin-1. Further, the inventors found an inverse relationship between claudin-1 levels and Smad4 levels in tumor lysates assessed by immunoblotting. They hypothesized that Smad4 may regulate the expression of claudin-1. The inventors tested the hypothesis by expressing Smad4 in claudin-1 expressing colon cancer cells that were Smad4-deficient, as demonstrated below and found that expression of Smad4 was sufficient to silence claudin-1 expression in both SW480 and HT29 cells. These studies are reported in detail in our recent manuscript (Shiou et al., 2007). Smad4 expression in the SW480 cells also results in increased expression of E-cadherin with redistribution of β-catenin to the cell membrane (FIG. 7) and results in decreased tumorigenicity (Muller et al., 2002b) (Schwarte-Waldhoff et al., 1999).

Figure 8:
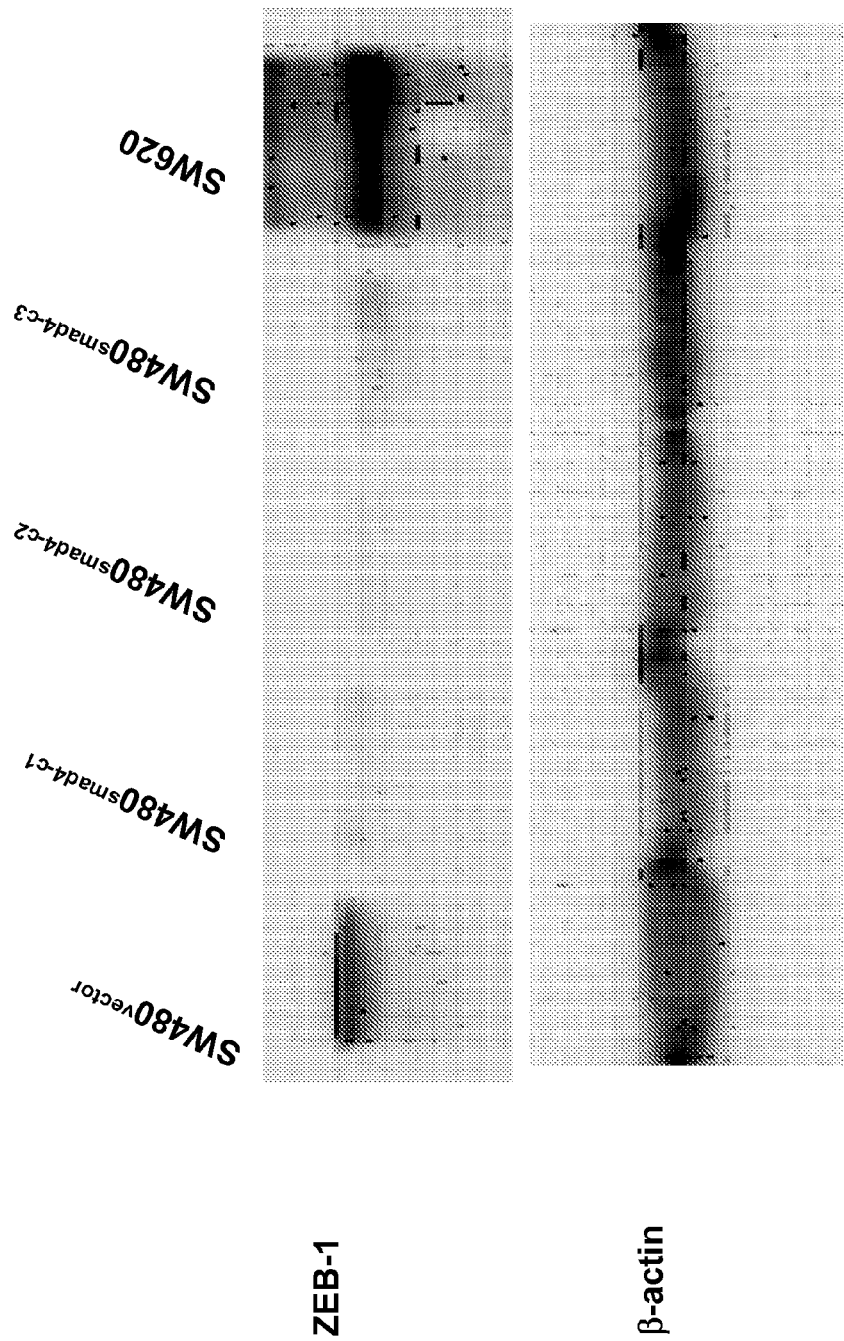
FIG. 8—ZEB-1 protein levels in Smad4-expressing clones of SW480 cells. Protein lysates were obtained from Smad4-expressing clones 1-3 of the SW480 cells and from vector transfected SW480 cells and SW620 cells. Steady state levels of ZEB-1 were determined along with β-actin to show equal loading of protein.

Given the above observation that Smad4 expression restores E-cadherin protein expression and membrane localization to the SW480 cells, the inventors then asked whether Smad4 expression altered the expression of ZEB1. As shown in FIG. 8, ZEB-1 levels are markedly suppressed in all three of the Smad4 expressing clones of SW480 cells as compared with vector transfected control cells. These data suggest that Smad4 expression regulates the availability of ZEB-1 and together with the observation that silencing of ZEB-1 is sufficient to restore E-cadherin expression suggests that this is the mechanism by which Smad4 expression restores E-cadherin expression in the SW480 cells.

Figure 9:
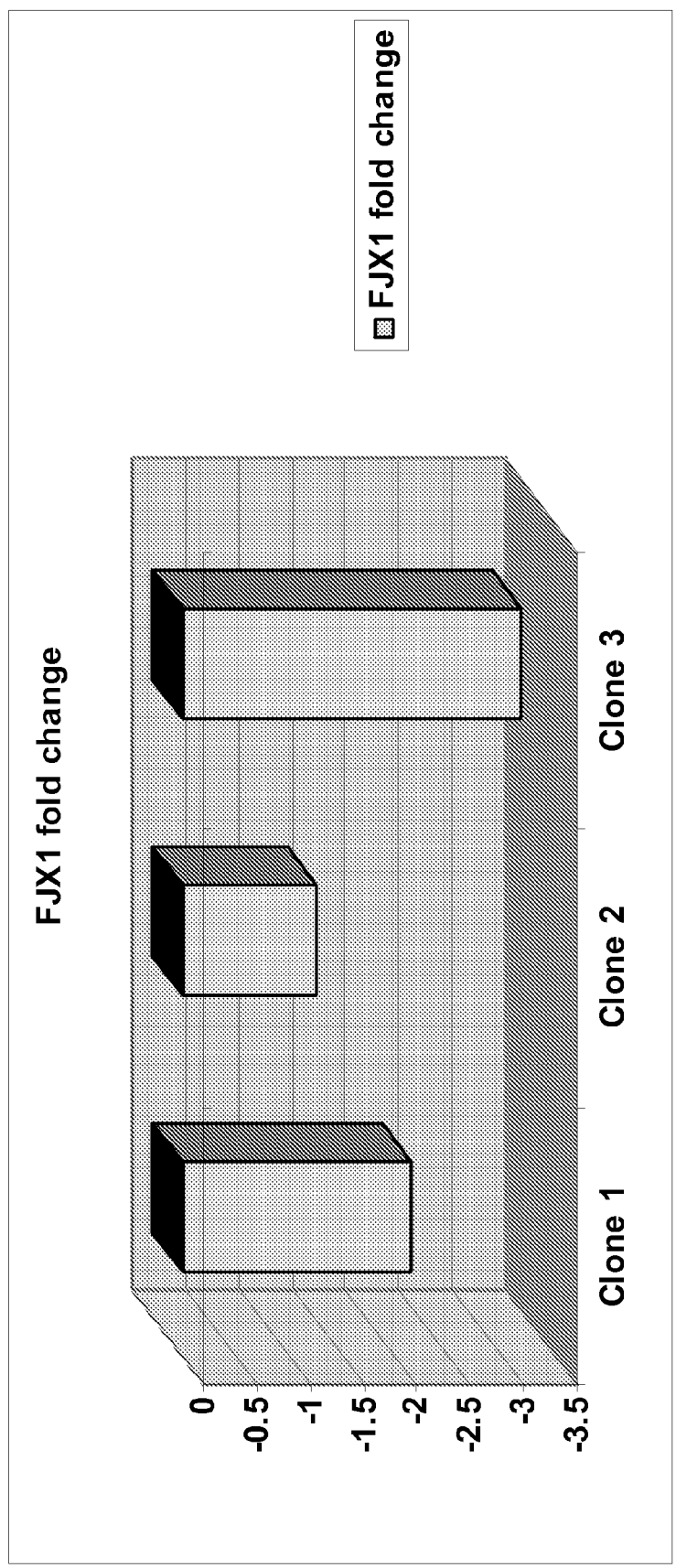
FIG. 9—qRT-PCR results of FJX1 expression in 3 SW480$^{Smad4}$ clones versus SW480 parental cells. Cells were grown to 70-80% confluence and RNA was harvested and purified bia the Rneasy™ kit from Qiagen. qRT-PCR was performed on the iCycler™ platform (BioRad) as described in the text. Raw expression values were normalized to the PMM1 housekeeping gene for the final analysis.

The inventors then asked whether expression of Smad4 may affect the expression of FJX1, since FJX1 is abundantly expressed in the parental SW480 cells. If Notch signaling and FJX1 contribute to the tumorigenic phenotype, conditions that reverse this phenotype may also inhibit Notch signaling and FJX1 expression. As noted above, Smad4 expression suppresses tumorigenicity, increases expression of E-cadherin, and decreases expression of claudin 1 and ZEB-1. The inventors also observed that expression of FJX1 is significantly reduced in the Smad4 expressing clones of SW480 cells (FIG. 9). At present, the inventors do not know whether this apparent reduction in FJX1 expression is due to decreased Notch signaling or through a separate mechanism.

Figure 10:
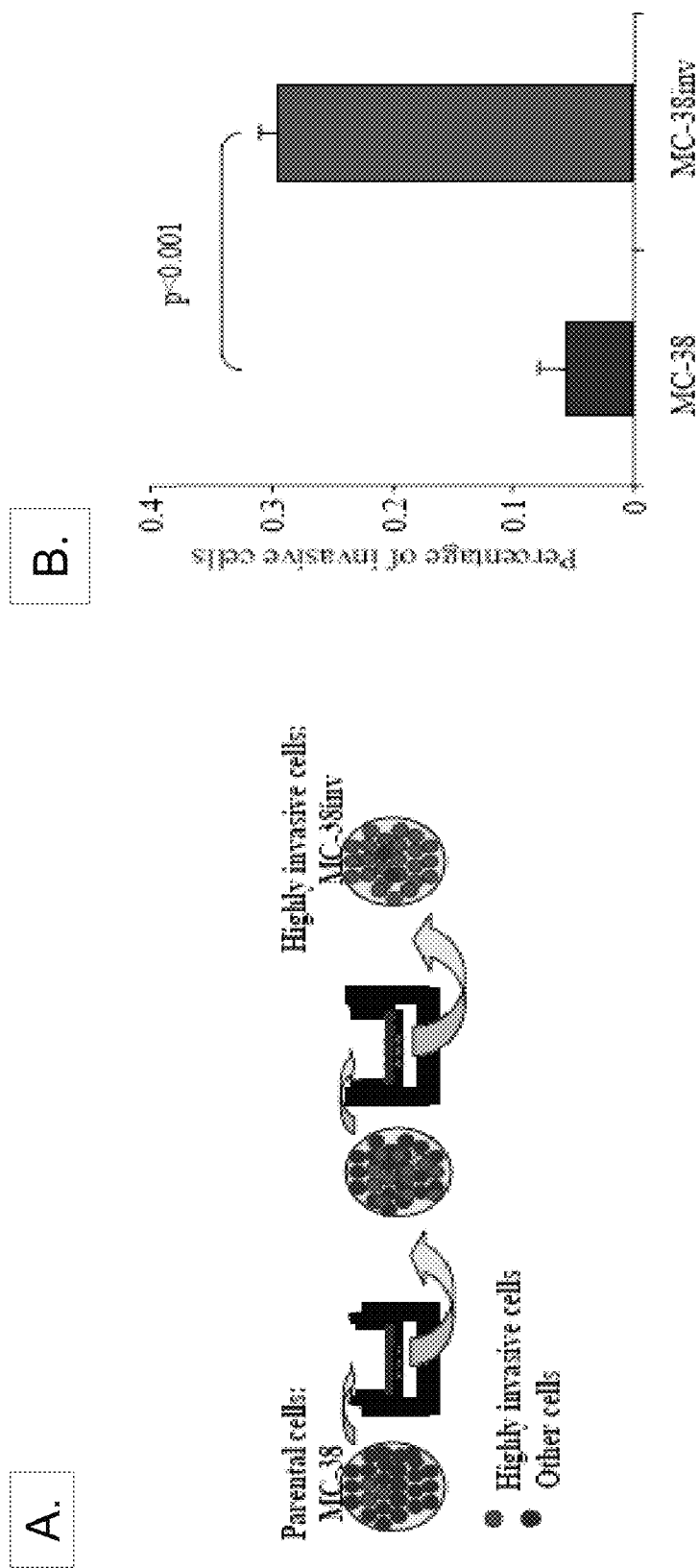
FIGS. 10A-B—Enrichment of invasive cells following in vitro selection.

A significant challenge in the analysis of microarray data from human specimens results from substantial within group variability, high volume read-outs and lack of statistical power. As such, although a strength of global gene expression analysis is lack of bias, discovery work emerging from these studies necessarily requires the application of a combination of statistical, bionformatic and biological tools. A second goal of the inventors has been to use the human microarray datasets to develop a gene expression signature for metastatic colon cancer. The inventors' approach to this challenge has been to use microarray analysis from a novel mouse model of colon cancer metastasis to inform our query of the human dataset toward a metastatic gene signature. For development of the mouse model, the inventors performed a series of experiments to enrich for metastatic cells in live, immunocompetent mice. First, the inventors stably transfected C57BL/6 derived mouse adenocarcinoma cells (MC-38) (Lafreniere and Rosenberg, 1986) with a luciferase reporter under control of the CMV promoter. Selection of highly invasive cells was accomplished in vitro through matrigel-coated Transwell filters (8 µm pore size) using a modified Boyden chamber invasion assay. Serial enrichment of invasive cell populations was made through replicate selections through Transwell filters. Bioluminescent imaging (BLI) was used to monitor both in vitro invasion through the matrigel-coated Transwell filters and in vivo metastasis. MC-38 cells selected for invasion demonstrated a 15-fold increase in the number of invasive cells compared to parental MC-38 cells (FIG. 10).

Figure 11:
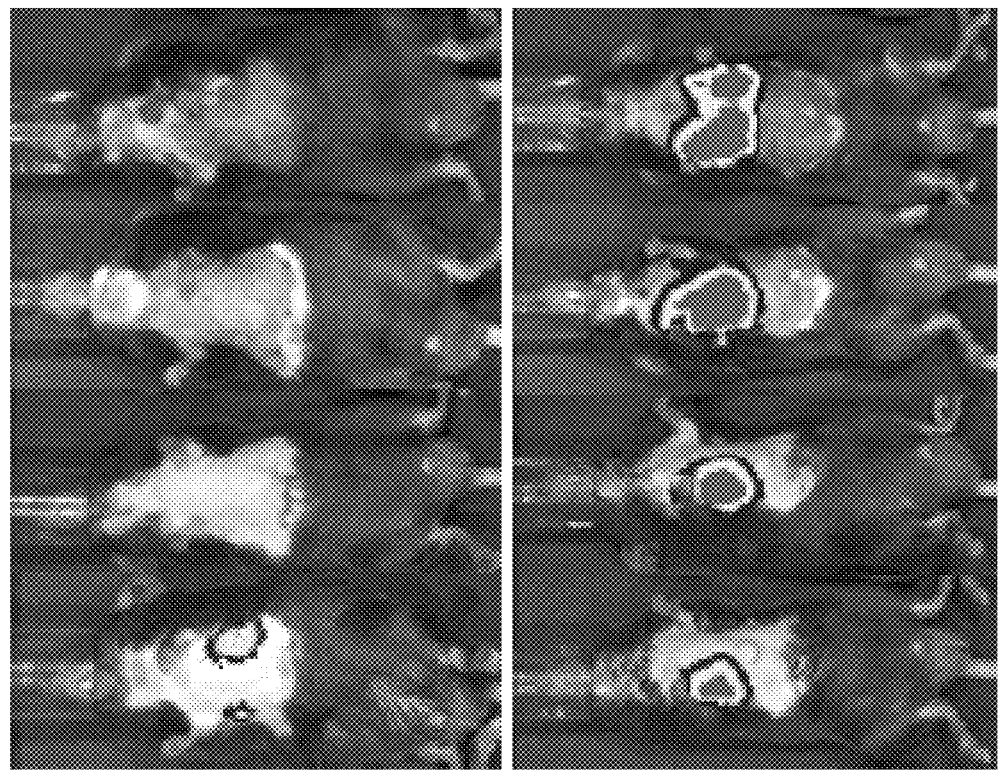
FIG. 11—In vitro selected cells have a high metastatic potential. Cancer cells expressing luciferase (MC-38 or MC-38inv, 2.5×10$^5$, 100 µl) were injected into tail vein of mice (n=10). Bioluminescent imaging (BLI) was performed at 1, 7, 14 and 21 days post-injection. Representative serial imaging of mice demonstrated increasing photon flux in the mouse injected with MC-38inv cells only (note different scale for mouse imaged at 21 days).
Figure 12:
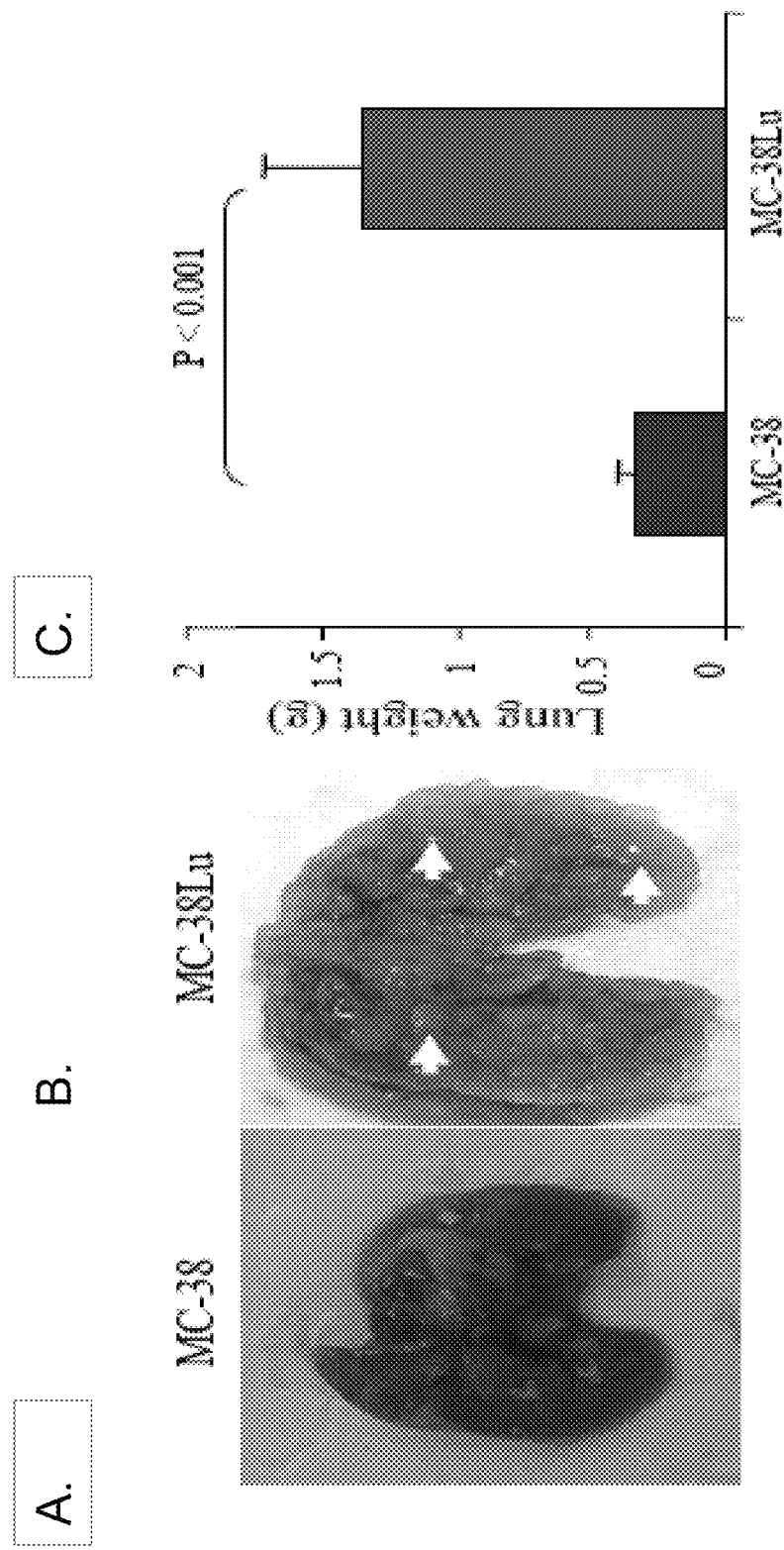
FIGS. 12A-C—In vivo selection of metastatic cells yields a stable phenotype. MC-38inv cells are metastatic, but these characteristics are not stable over time. The inventors further selected MC-38inv cells by in vivo passage, expanding cells derived from lung nodules in tissue culture (MC-38Lu) and re-injected through the tail vein of mice. Autopsies were performed 3 weeks following injection.

Subsequently, equal numbers of MC-38 parental cells or invasion-enriched cells (MC-38inv) were injected into tail veins of C57BL/6J mice and metastatic spread was followed non-invasively for three weeks using live mouse BLI (10 mice per group) (FIG. 11). At necropsy, the average number of pulmonary metastases in the group injected with MC-38inv cells was 14-fold greater and lung weight per mouse 3-fold greater than the group of mice injected with parental MC-38 cells (not shown). A cell line (now called MC-38Lu) was then established from these lung metastasis. Three weeks following injection of MC-38Lu cells into the tail vein of C57BL6 mice, the number of resulting pulmonary metastatic nodules was too numerous to count and the lung weight was increased 4.3-fold over parental MC-38 injected mice (FIG. 12). Thus, MC-38Lu cells were found to be not only more pronounced in their metastatic phenotype as compared with MC-38inv cells but this phenotype was made stable by the in vivo passaging.

In collaboration with the VUMC Biostatistics and Bioinformatics departments, the inventors performed global gene expression analysis on MC-38 and MC-38Lu cells (n=3 replicate clones per group) using microarray and intersected the set of genes significantly up or downregulated in metastatic vs. non-metastatic cells with those genes identified as being up or downregulated with increasing stage (vs. adenoma) from the human specimen study. Briefly, mouse and human microarray experiments were performed on Affymetrix platforms, Mouse430_2 and HG-u133_plus_3, respectively. After obtaining the microarray data generated by the Microarray Suite Software (MAS) version 5.0, the inventors removed 19361 and 18273 probe sets that did not have a present call in any of the 6 mouse samples and the 38 human samples. Remaining data were log transformed and globally normalized. Normalization was performed by subtracting the signal of a particular probe set in a particular experiment by the average signal across all the probe sets in that experiment. This is done so that the global average signal is the same across all experiments. The inventors used the siggene package in bioconductor (world-wide-web at bioconductor.org) to identify the differentially expressed genes between the two types of mouse samples, and the genes that are significantly correlated with the stage data in the human samples. 696 probe sets unambiguously representing 370 unique Ensembl genes were identified in the human experiment with a false discovery rate (FDR) of 0.10. 780 probe sets unambiguously representing 526 unique Ensembl genes were identified in the mouse experiment with an FDR of 0.02. Similarly, the inventors also intersected microarray data from the inducibly transforming rat intestinal cell line RIE:iRAS that are maximally induced to undergo EMT following treatment with Ras and TGF-β (Sheng et al., 2000). In this dataset, 1399 probe sets unambiguously identified 715 unique Ensembl genes with using an FDR of 0.01. The inventors picked different FDRs so that the number of human genes and mouse genes are comparable and to allow us to use more stringent criteria in the cell culture systems where sample variability can be controlled.

Figure 13:
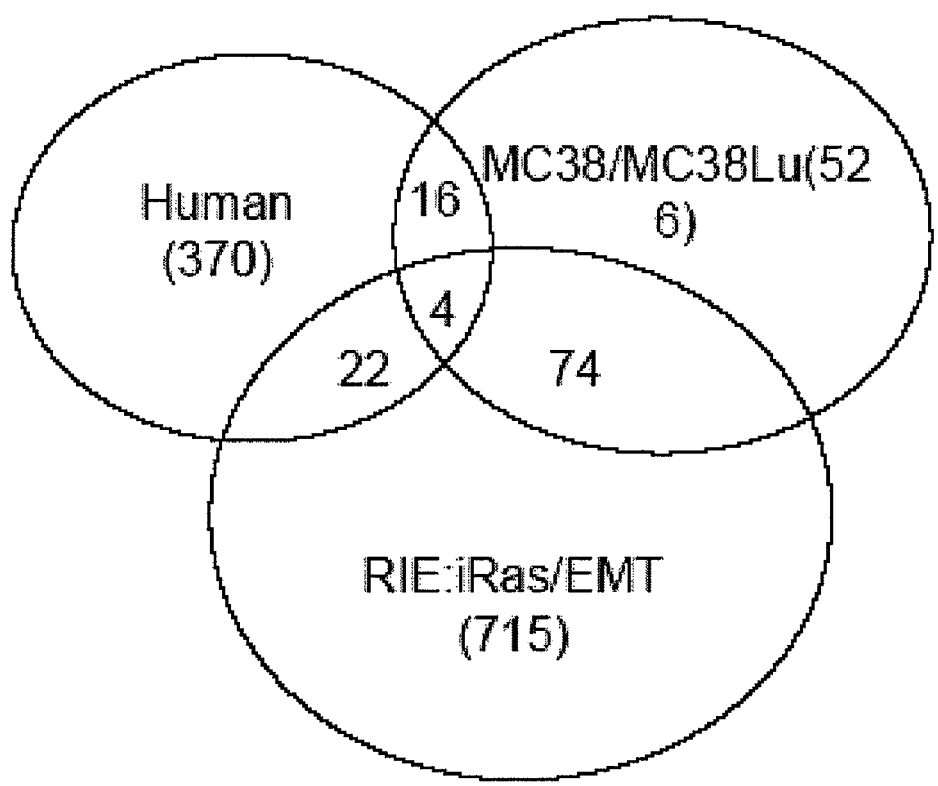
FIG. 13—Diagram showing potential metastatic phenotype for colon cancer cells. Overlapping datasets reveals potential signature for metastatic phenotype in colon cancer cells. False discovery rate (fdr) as follows: human=0.1, MC-38/C-38Lu=0.02, RIE:iRas/EMT=0.01.

In order to perform cross-species comparison, the inventors next mapped the mouse genes to their human orthologs based on the Ensembl annotation. Among the 526 mouse genes, 435 could be mapped through a "one to one" mapping. The inventors found 20 genes that are common between the 370 human genes identified from the human experiment and the 435 human orthologs of the genes identified from the mouse experiment. Interestingly, 10 of these 20 genes map to developmental pathways (MYH10, COL1A1, COL12A1, EPAS1, POSTN, TNC, NPR3, PDLIM7, GYS1 and ADAM12), 6 map to cell adhesion pathways (ARHGDIG, COL12A1, POSTN, TNC, THBS2 and ADAM12) and 6 are known metastases-related genes (COL1A1, FAP, EPAS1, POSTN, TNC and ADAM12). Four genes (COL1A1, POSTN, ARHGDIG, and Col12A1) represent the intersection between all three groups (FIG. 13).

Figure 14A:
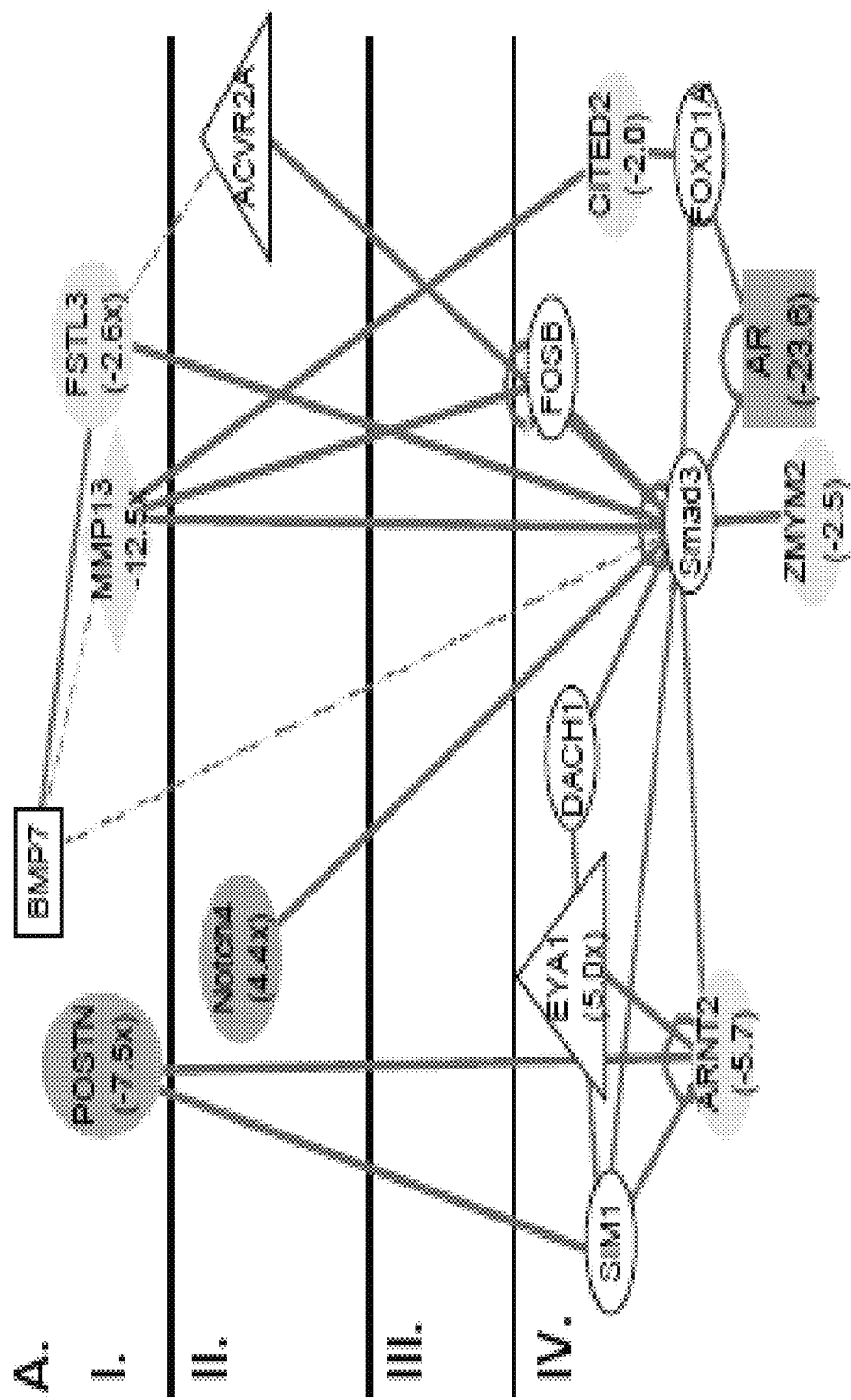
FIGS. 14A-B—Signature networks for colon cancer metastatic phenotype. Two networks generated from the mouse signature are shown, linking signature genes with Notch, TGF-β/BMP and Wnt pathways. (I) Indicates extracellular domain (II) Indicates plasma membrane domain (III) Indicates cytoplasmic domain (IV) Indicates nuclear domain. Green color indicates downregulation vs. non-metastatic cells (FIG. 14A) (POSTN=osteopontin, MMP13, FSTL3=Follistatin like ligand3, AR=Androgen receptor), CITED2, ZMYM2=MIM-type Zinc finger, ARNT2=HIF2β) (FIG. 14B) OSTF1=osteoclast stimulating factor 1). Red color indicates upregulation in vs. non-metastatic cells (A) (Notch4) (B) COL1A1—Collagen 1A, FAP=Fibroblast activation protein, VDR=Vitamin D3 receptor. Solid lines indicate direct interactions and dashed lines indicate indirect interactions.
Figure 14B:
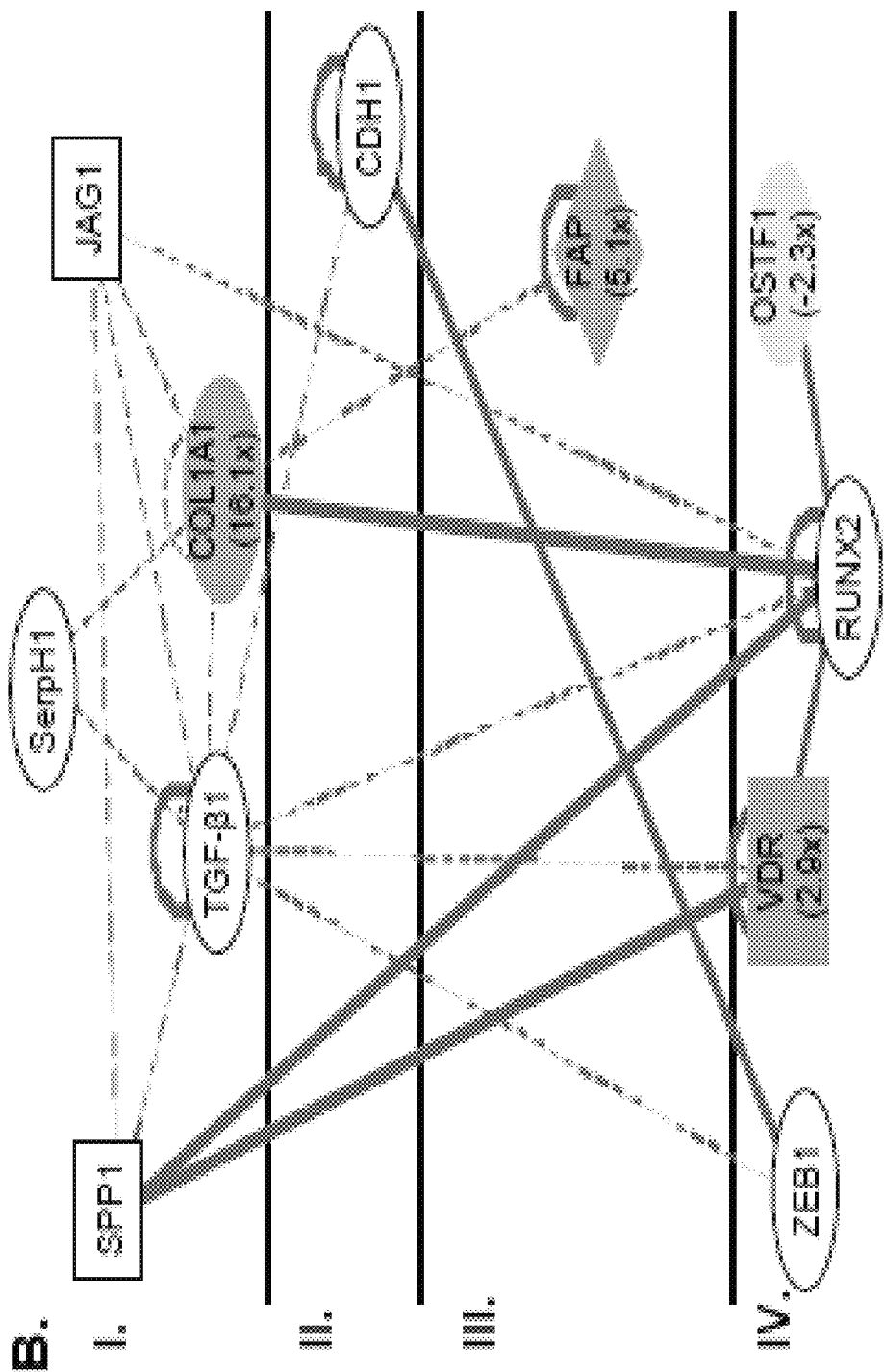

Thus, the twin challenges of high sample variability and low power in the evaluation of human microarray datasets have been met by intersection with more uniform datasets that afford lower false discovery rates (0.02 and 0.01, respectively). Intersections of the mouse and rat datasets with the human dataset were used to inform the development of a colon cancer gene expression signature that is associated with TGF-β mediated EMT and a metastatic phenotype. In ongoing studies, the inventors are evaluating links between this putative metastatic signature and patient outcomes. In the meantime, we have used Ingenuity Pathway Analysis™ to identify links between this signature and the Notch and/or TGF-β/BMP and Wnt signaling pathways. FIG. 14 shows the results of two such networks from the mouse datasets linking Notch pathway members Notch4, Jagged1 and Dach1 to signature related genes Col1A1 and POSTN and to other genes of relevance to this study including Zeb1 (TCF8), E-cadherin, BMP7, Smad3, TGF-β and Runx2.

To summarize, several lines of evidence in the published literature implicate Notch signaling as important in colorectal cancer, although its roles and impact on tumor phenotype are incompletely understood. The inventors find evidence for increased Notch expression, and downstream target genes FJX1 and Hey1 in human colorectal cancers as compared with adenomas and with normal colon mucosa in gene expression arrays of human colorectal cancers. The inventors also have provided evidence that shifting colon cancer cells from the mesenchymal phenotype to the more epithelial phenotype is accompanied by downregulation of FJX-1a downstream target of Notch, thus suggesting that Smad4 expression may disrupt Notch signaling. Taken together, these findings suggest that a complex interaction of Notch, BMP/Smad signaling, Wnt signaling and ZEB1 have marked effects on determining colon cancer cell phenotype in a potentially regulated manner. Finally, inhibition of COX2 with celecoxib in a clinical trial resulted in decreased mRNA expression of the Notch target, FJX1. Since COX2 activity and its products such as PGE2 and other prostaglandins play important roles in cancer cell survival and angiogenesis, this may link Notch signaling to these important roles in cancer.

Example 2

Human colorectal cancer microarray analysis. As discussed above, the inventors analyzed rectal tumors from 16 patients with rectal cancer via Affymetrix GeneChip microarray (Affymetrix U133 Plus 2.0 gene chip microarray platform). These patients underwent endoscopic pinch biopsies both before and after one week of celecoxib treatment (400 mg twice per day) and before any other treatment. The effect on COX-2 activity was confirmed by demonstrating a significant decrease in the urinary metabolite of $PGE_2$, $PGE_M$, among these patients when comparing pre-versus post-Celebrex treatment as we have reported in Johnson et al. (2006) (manuscript included in appendix). The tumor samples submitted for microarray analysis included: 3-stage 1 cancers, 7-stage 2 cancers, and 6-stage 3 cancers.

Initial evaluation uncovered 13 genes whose expression was significantly different in comparing pre-treated to those after Celebrex® treatment (Table 6). Validation of fjx1 expression by quantitative real-time polymerase chain reaction (qRT-PCR) was carried out in a random selection of 5 of the 16 rectal cancer patients, and fjx1 mRNA was verified down-regulated (range: 2.5-17.5-fold decrease) in four of the five rectal cancers after Celecoxib treatment (not shown). The identification of the Notch pathway gene, fjx1, in this study, along with recent evidence of Notch involvement in colorectal epithelial differentiation and carcinogenesis, led us to examine this pathway more closely in colorectal cancer specimens.

TABLE 6

Genes Correlating with Urine PGE-M Following Celecoxib Treatment
Gene Name fjx1
rhov
kctd3
c1qtnf6
ctnnbip1
c18orf1
postn
senp5
ulbp2

Figure 15:
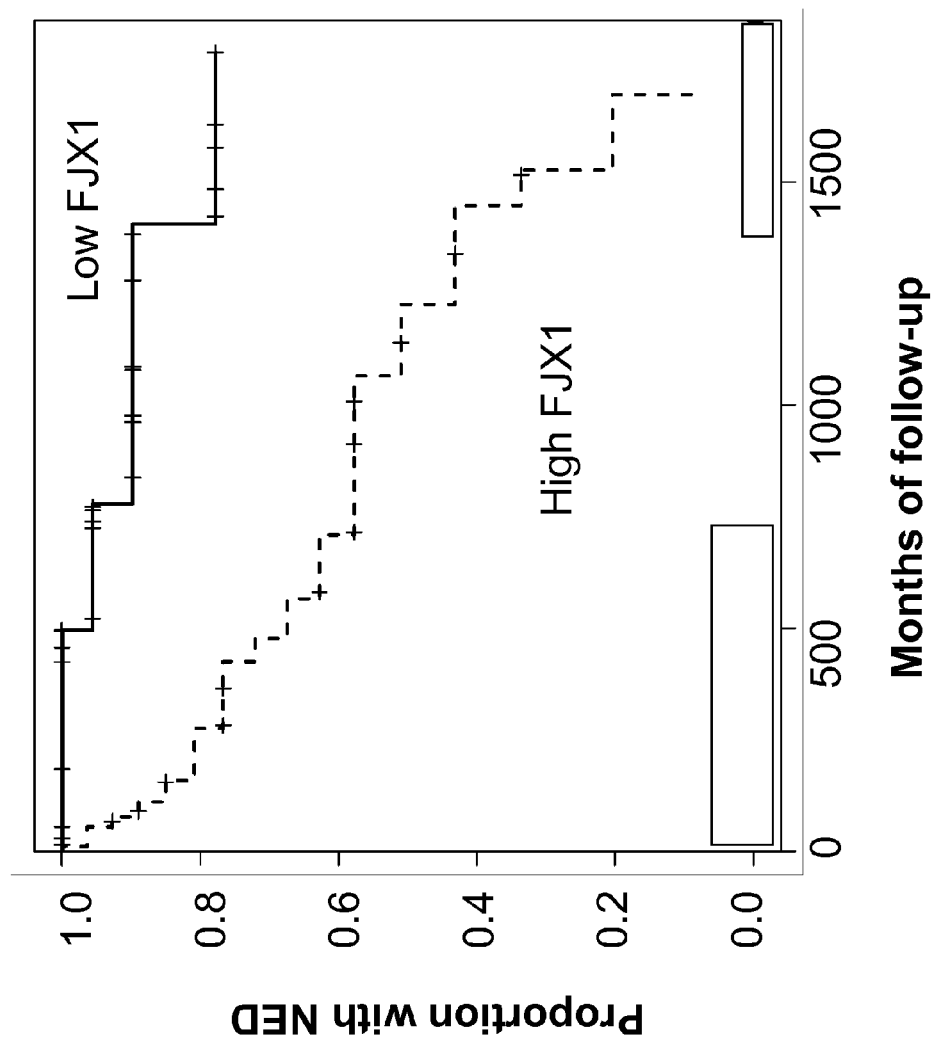
FIG. 15—Fjx1 expression in tumors confers poor prognosis in CRC. Kaplan-Meier plot showing follow-up of 60 Stage 1-4 CRC patients with tumor fjx1 expression greater than (solid line) or less than (dotted line) th mediam across all patients. The proportion of patients with No Evidence of Disease (NED) is plotted over time. Log rank statistic: p=0.004.

Subsequently, the inventors have accumulated expression data on a total of 65 patients from adenoma to Stage 4. To review our microarray data analysis: 60 colorectal cancer patient samples and 5 adenoma patient samples available through our collaboration in the GI SPORE were obtained. RNA was isolated and submitted for hybridization on the Affymetrix U133 Plus 2.0 gene chip microarray platform. The raw expression data was obtained and converted to expression values using the Affymetrix function in (world-wide-wb at bioconductor.org). The Affymetrix function allows for common options to convert probe level data into expression values, these options include: (1) background correction, (2) normalization (RMA method), (3) probe specific background correction (e.g., subtraction of mismatch probes), and (4) summarization of the probe set values into one measure of expression. High and low expressers of fjx1 were determined in relation to a median level of fjx1 expression and Kaplan-Meier survival curves were generated for high and low expressers. Tests for the difference between survival curves for the high and low fjx1 expressers were done using a log rank test statistic for the fjx1 probe (p=0.004) (FIG. 15). As can be seen, by 3 years of follow-up (1095 days) approximately 50% of patients with high fjx1 expression have recurred/died whereas 90% of patients with low fjx1 expression remain disease free. Therefore, high expression of fjx1 is associated with a worse disease-free and overall survival.

Figure 16:
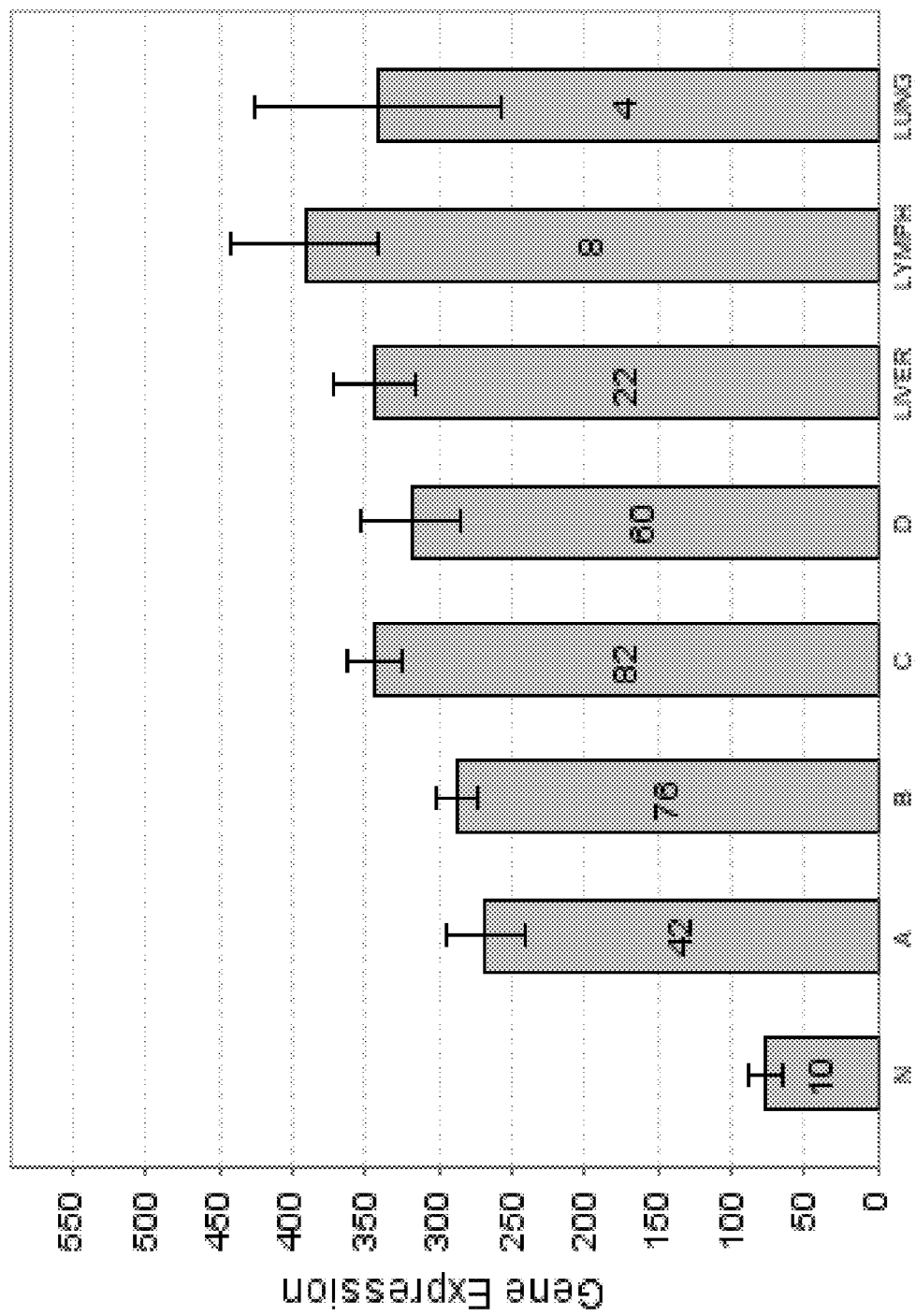
FIG. 16—Validation of upregulated fjx1 expression in adenocarcinoma. Average fjx1 expression levels in a >200 patient CRC microarray database. Relative levels from normal colonic mucosa. Duke's stage A-D, and liver, lymph node and lung metastases as shown.

Independent validation of fjx1 overexpression in late stage CRC. The inventors recently queried an independent human colorectal cancer gene expression array database (Affymetrix U133 2.0 Array) representing 260 colon adenocarcinomas to determine whether fjx1 expression levels are, in fact, increased in primary colorectal cancers (stages A-D) and in metastatic colorectal cancer lesions as compared with normal colonic mucosa (N) (FIG. 16). These data indicate that fjx1 expression was on average 3-5× increased in colon carcinomas when compared with normal colonic mucosa in this independent test set and that expression of fjx1 is similarly elevated in liver, lymph node and lung metastasis in CRC patients.

Further, in a second independent test set of human cancer, the inventors queried the Gene Expression Omnibus (GEO) database at the NCBI to determine the levels of fjx1 expression in breast cancer (world-wide-web at ncbi.nlm.nih.gov/geo/query/acc.cgi?acc=GSM152678). They found that Fjx1 expression is increased in a stage-specific manner in breast cancer, and stage 0 demonstrates a marked difference from advanced carcinoma. They have also noted that fjx1 expression is increased in late stage colorectal adenocarcinoma versus normal adjacent tissue of colonic adenoma in a parallel microarray experiment using an independent platform (Applied Biosystems/ABI) (p=0.03) (data not shown).

Figure 17:
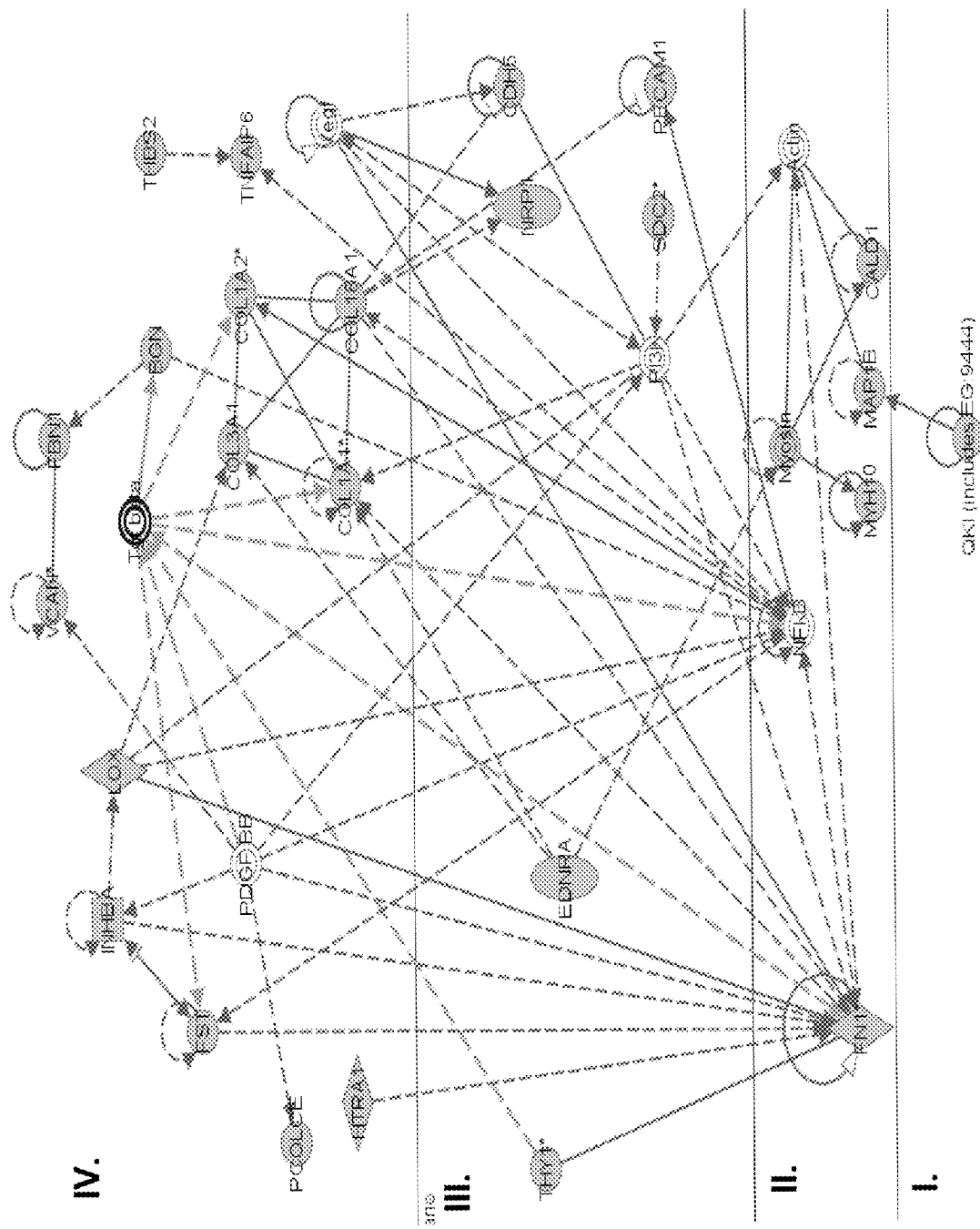
FIG. 17—Top network of fjx1 co-regulated gene linked to regulation of cell motility. IPA network analysis of top 100 genes regulated in coordination with fjx1 organized by cellular location (I) nuclear, (II) cytoplasmic, (III) plasma membrane associated, and (IV) extracellular. Shaded nodes are differentially regulated in coordinate fashion with fjx1 in CRC. Links to TGF-β signaling pathway are highlighted.

Next, expression data were examined to determine which changes are significantly correlated with fjx1 expression. The inventors examined the association between fjx1 high and fjx1 low expressers and all other genes on the platform using a permutation test approach. The top 100 genes as ranked by permutation test and fold change were then plotted using the heatmap function in the statistics package R (world-wide-web at r-project.org/). Eighty-four (84) named genes resulted and were analyzed by Ingenuity® Pathways Analysis (world-wide-web at ingenuity.com/). The top associated network was enriched for genes involved in cellular movement (p<0.006) and in organismal development and function (p<0.005) (FIG. 17). As can be seen in the figure, TGF-β is a central node of this network containing genes involved in planar cell polarity, Notch signaling, and cell movement. Important to note are the TGF-β and BMP connections in this analysis, in particular, (follistatin (BMP antagonist), Inhibin P A, HtRA1 (HtRA serine peptidase 1, a BMP and TGF-β antagonist)), several collagens (collagen 18A), an atypical cadherin (CDH5 or Cadherin 5, type2, VE-cadherin), and NRP1 (neuropilin 1, upstream from Notch in angiogenesis, personal communication with T. Kume, VUMC and reviewed (You, 2005). Also, CDH5 is known to be downregulated by Col18A and CDH5's assembly is regulated by cdc42 (which is involved in the Rho-Rac pathway that is thought to be important for PCP, personal communication with E. Lee and S. Hanks, VUMC, and reviewed in (Shichiri, 2001) and (Kaibuchi, 1999).

Given the observed increase in the fjx1 in colorectal carcinomas and evidence that both fjx1 and its *Drosophila* homologue, fj, are regulated by Notch (Rock, 2005), the inventors next asked whether there was other evidence of increased Notch signaling in colorectal cancers assessed by expression profiling in this experiment. Genes were rank-ordered by their permutational p-value and fold-change in relation to fjx1 expression from the aforementioned microarray experiment. Amongst the genes most significantly changed according to fjx1 expression are 20 genes as they relate to planar cell polarity, TGF-β and Notch signaling, and cell movement (Table 7). Of note, are dachsous 1, which is a large cadherin interacting with four-jointed in *Drosophila* (reviewed in Rock, (2005)), and notch 3 which we hypothesize plays a role in cell-cell interaction or differentiation in colon adenocarcinoma. Both dachsous 1 and LATS 2 are downregulated (−22 and −43 fold respectively) while Hes 1 is up-regulated by 20 fold. The inventors have recently shown that Slug regulates E cadherin in intestinal epithelial cells (Schmidt, 2005), and here they find that Snail 2 (a.k.a. Slug) is down-regulated by 66 fold. Particularly interesting is Id1 (a novel BMP target) which may be down-regulated by Herp2 after it is stimulated by the active intra-cellular Notch domain.

TABLE 7

Coordinate Regulation of Genes with fxj1

| Signaling Pathways | | Cellular Processes | |
|---|---|---|---|
| TGF-β Superfamily | Notch | Planar Cell Polarity | Cell Movement |
| Inhibin Beta A | Hes 1 | Protocadherin 17 | RAB 31 |
| HTRA1 | Notch 3 | Snail 2 (Slug) | LAMA 4 |
| Fibronectin 1 | ADAM12 | Cdh5 | Collagen Iα1 |
| Follistatin | Neuropilin 1 | Dachsous 1 | Collagen Iα2 |
| Thrombospondin | Id1 (cross talks with TGF-β) | LATS 2 | Fibronectin 1 |

Figure 18:
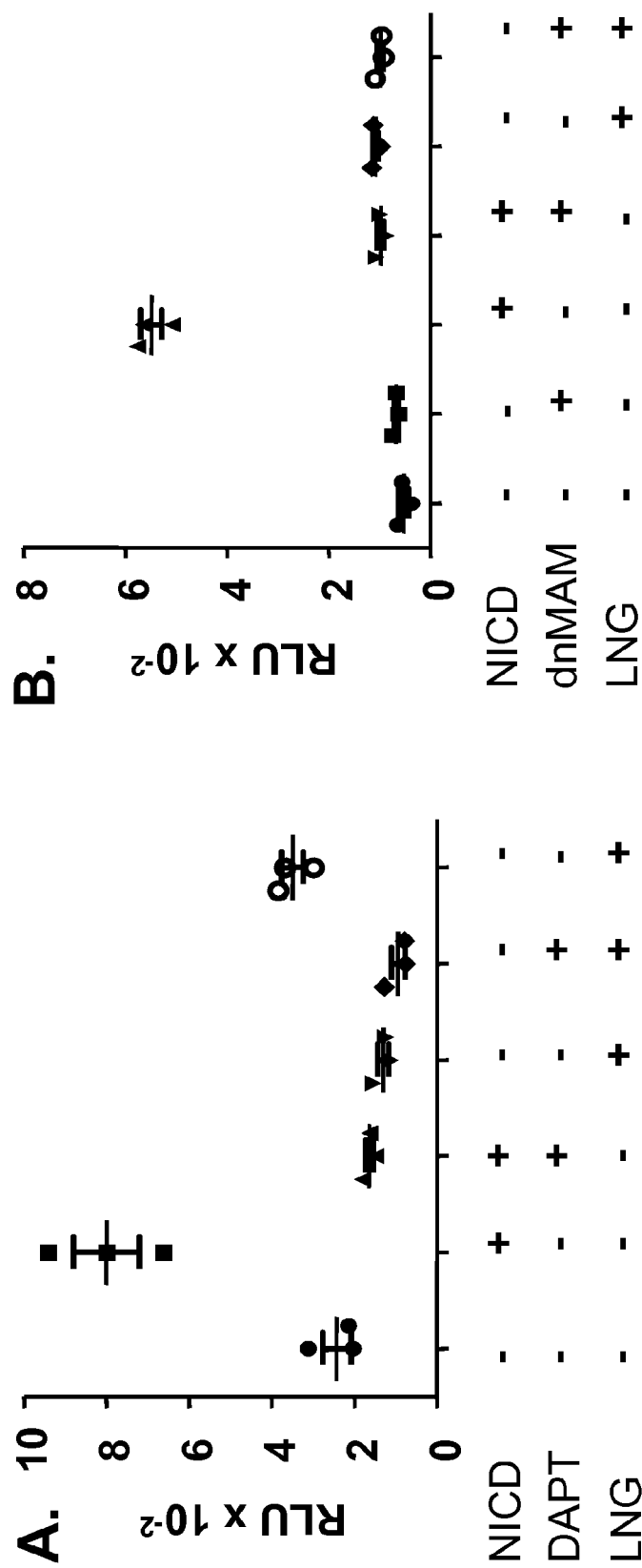
FIGS. 18A-B—Experimental inactivation of Notch pathway signaling in HEK293 cells. Transient transfections of cells was carried out using a Notch promoter reporter plasmid (4xCSL) and a control reporter (pRL-tk). The Relative Light Units (4xCSL/pRL-tk) are plotted for each treatment group.
Figure 19:
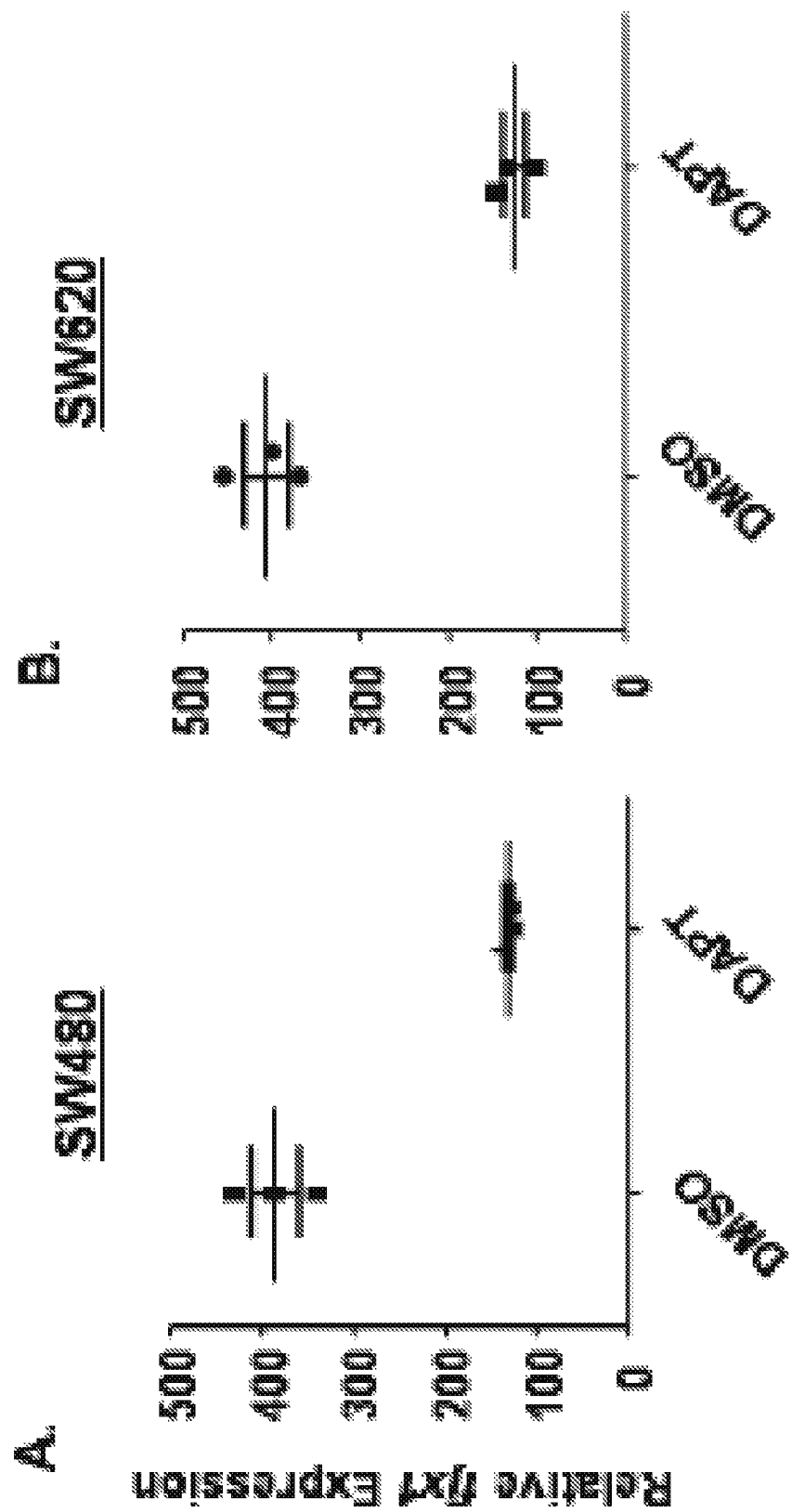
FIG. 19A-B—Inhibition of Notch signaling causes a reduction in fjx1 expression in colon cancer cells. Fjx1 expression levels as determined by qRT-PCR in (FIG. 19A) SW480 and (FIG. 19B) SW620 colon cancer cells following treatment with the γ-secretase inhibitor DAPT.

FJX1 expression in colon cancer cells. In preliminary studies examining the role of fjx1 as it relates to Notch signaling in CRC, the inventors have assessed expression of fjx1 mRNA in several human colon cancer cell lines and found abundant expression of fjx1 in both SW480 and SW620 cells (in comparison with colon adenomas), and less abundant expression in HT29 cells as determined by qRT-PCR (data not shown). Since four-jointed in *Drosophila* is regulated by Notch signaling, and mouse fjx1 expression appears to be a target of Notch regulation, the inventors predicted that inhibition of Notch signaling would inhibit fjx1 expression in colon cancer cells. A reliable pharmacological method of inhibiting Notch signaling is to block release of the Notch intracellular domain through inhibition of γ-secretase activity (van Es, 2005). A complementary genetic method of Notch inhibition is through the use of a truncated, dominant negative construct of Mastermind or "dnMAM" (pCS2-Myc 1-30aa Mastermind a gift from K. A. Jones, Ph.D., the Salk Institute, La Jolla, Calif.) (Fryer, 2002). The dnMAM is mutated such that it cannot form a functional RBPJ complex and therefore, cannot activate the Notch responsive promoter. Using a Notch-responsive reporter gene containing a promoter with 4 contiguous CSL binding sites linked to luciferase (4xCSL-Luc) (Ong, 2006), the inventors have demonstrated specific Notch pathway inhibition using the γ-secretase inhibitor, DAPT, in HEK293T cells (FIG. 18A) and in SW480 cells (not shown) and dnMAM mediated Notch pathway inhibition in HEK293T cells (FIG. 18B). The inventors have also used DAPT treatments of SW480 and SW620 cells (200 nM for 16 hrs) to block expression of fjx1 in response to Notch signaling (FIG. 19). While these data demonstrate that fjx1 expression levels are responsive to DAPT and are suggestive of a Notch specific effect, the inventors cannot rule out that non-specific effects of DAPT on proteins such as E-cadherin (see background; (Kopan and Ilagan, 2004) may also contribute to altered fjx1 expression.

Figure 20:
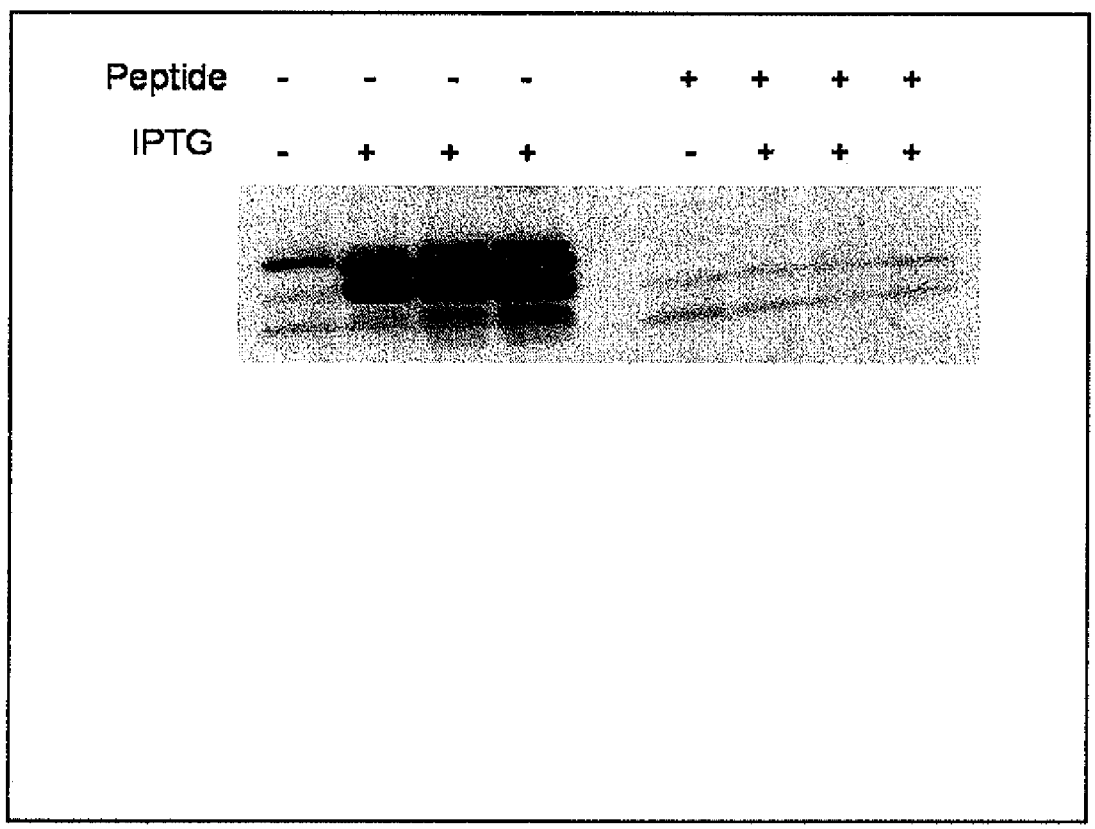
FIG. 20—Polyclonal rabbit antisera raised against fjx1 peptide recognizes inducible recombinant fjx1 protein. Inducible fjx1 was overexpressed using IPTG in BL21 (DE3) plysS bacterial cells. Following electrophoresis, protein lysates were immunoblotted for FJX with and without challenge by 3 μg/μl FJX specific peptide as indicated. The fjx1 cDNA was obtained from the Vanderbilt Microarray Core (clone ID 5482332) in the pOTB7 backbone. To engineer EcoR1 and Sal1 restriction sites onto a 1.0 kB FJX1 fragment (nucleotides 548-1510), clone 5482332 was amplified using oligonucleotides FJX1-S (5'-GATCGAATTCGTG-CACGGGGGCGTCTTCTGG-3') (SEQ ID NO:3) and FJX1-AS (5'-GATCGTCGACCTCCCGGTGACAC-TAAGTCCCAGAC-3') (SEQ ID NO:4) using PCR. The resulting product was digested with EcoR1 and Sal1 and cloned into the EcoR1/Sal1 sites of pET-44A to create pET-44A-FJX1. pET-44A-FJX1 was sequenced and transformed into BL21(DE3)plysS. Recombinant FJX1 protein was induced with IPTG for 1, 2 and 3 hrs.
Figure 21:
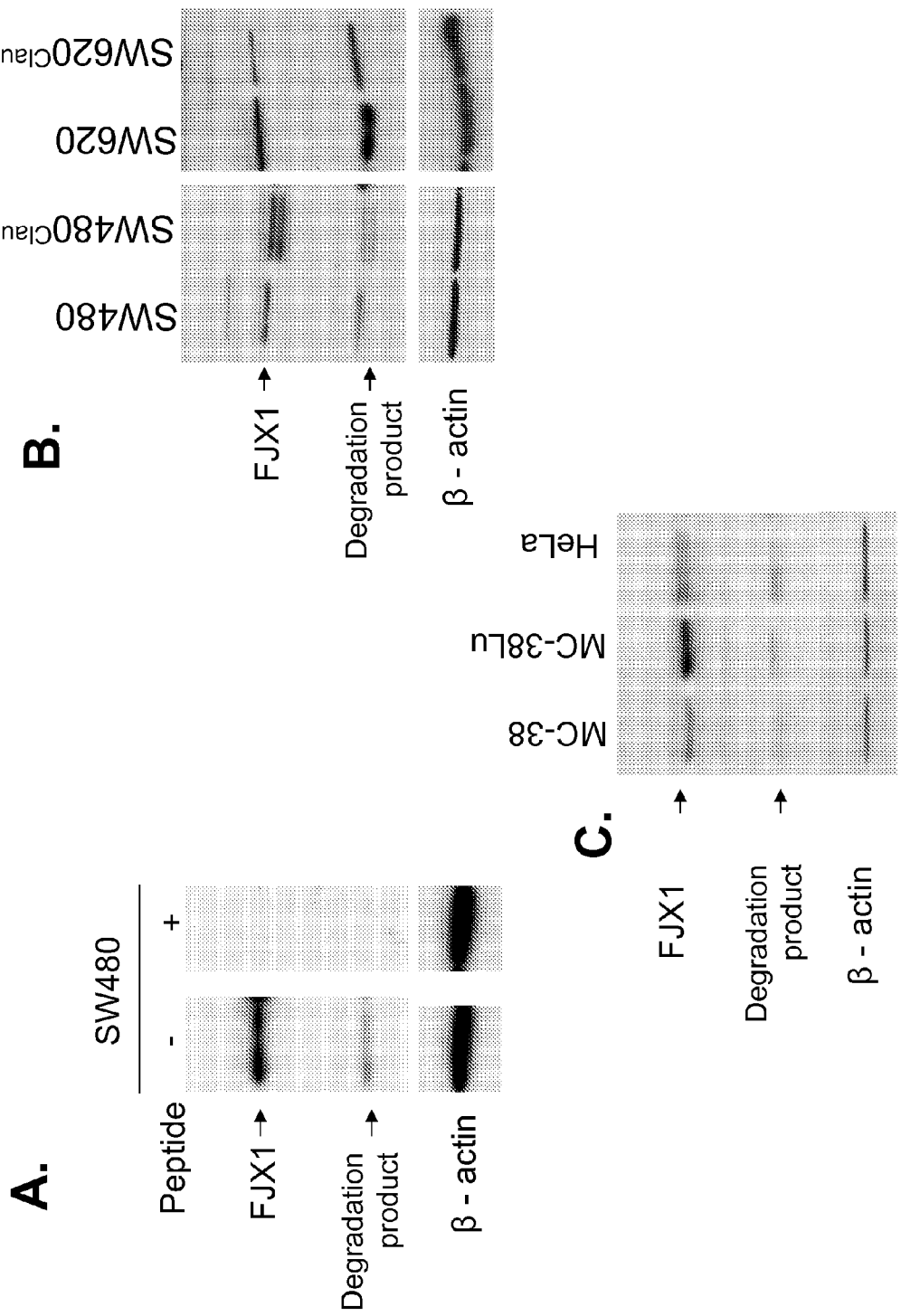
FIGS. 21A-C—Polyclonal rabbit antiserum detects FJX specific band in human and mouse colon cancer cell lines.
Figure 22:
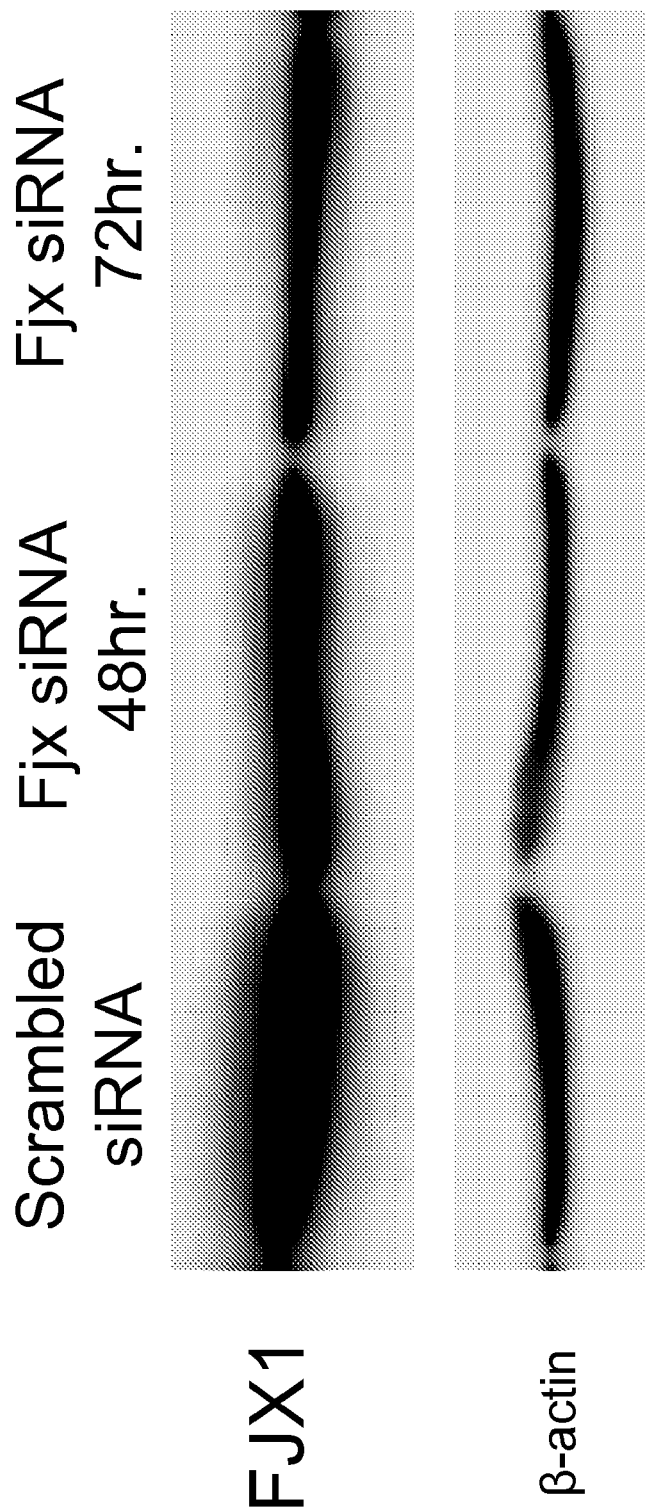
FIG. 22—Knockdown of fjx1 protein expression in HEK293T cells. HEK293T cells were transiently transfected with either 10 nM of a non-specific siRNA pool or with 10 nM of fjx-specific siRNA pool and FJX protein levels were assessed at 48 hr and 72 hr post-treatment as indicated.

The inventors recently contracted with Covance Innovative Antibodies, Inc. to produce a polyclonal antibody to a peptide sequence specific to the FJX1 protein. To accomplish this, they chose the optimum predicted peptide sequence, CVFR-ERTARRVLE (amino acids 365-377), which is just proximal to the C-terminus of the 450 amino acid full-length protein, identical between mouse, rat and human FJX1 and otherwise unique in the NCBI Blast database. They have successfully characterized the rabbit antisera and have a high titer antibody which recognizes a unique protein band corresponding to both recombinant (FIG. 20) and endogenous (FIG. 21) expressed FJX1. Using the novel antibody, the inventors can now demonstrate inhibition of FJX1 expression after treatment of HEK293T cells with siRNA oligonucleotides directed against fjx1 (FIG. 22). The inventors have had more effective reduction of expression of target genes using shRNA as they have previously demonstrated for silencing of claudin-1 in SW620 cells (Dhawan, 2005).

Figure 23:
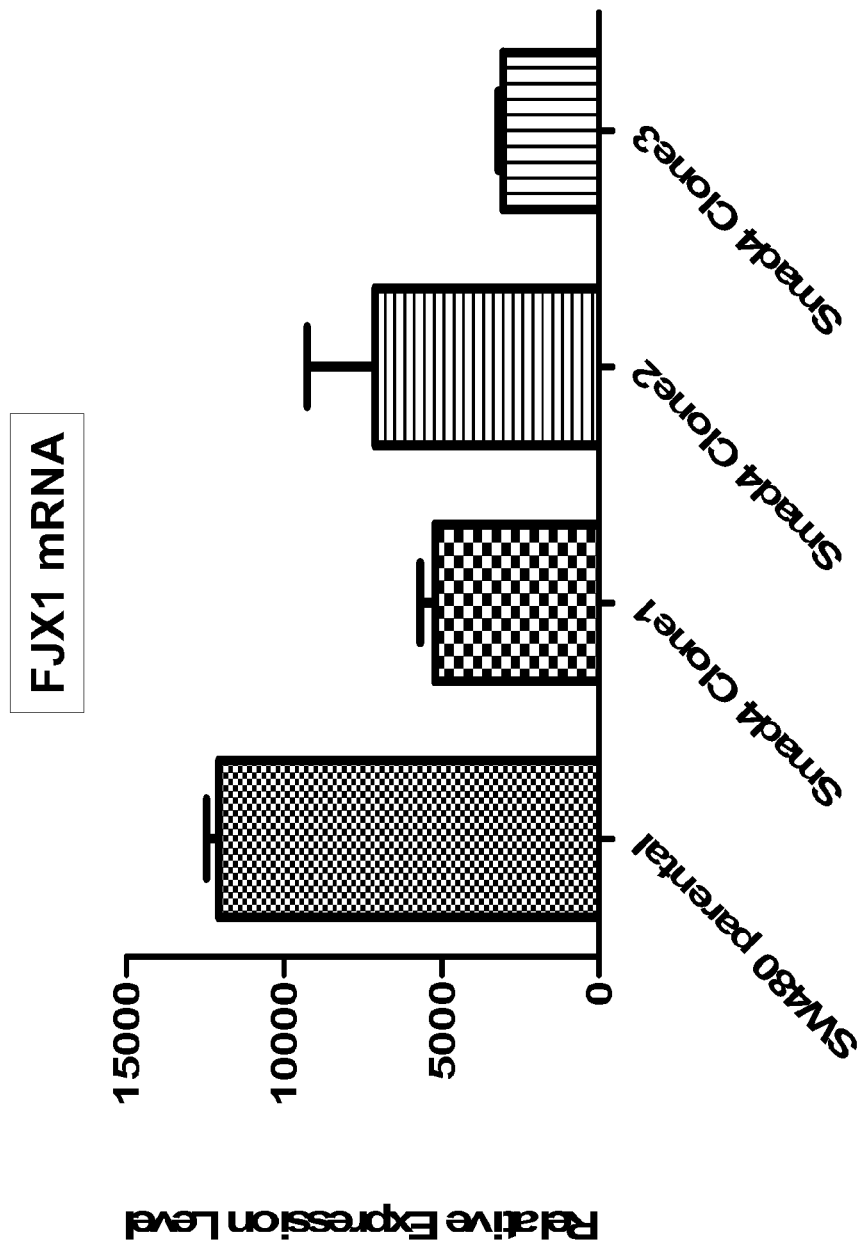
FIG. 23—Downregulation of fjx1 following re-expression of Smad4. SW480 cells were stably transfected with Ad-Smad4 (Shiou, 2007) and fjx1 levels were determined by qRT-PCR. Raw expression values for fjx1 are shown normalized to the pmm1 housekeeping gene.

The inventors next asked whether expression of Smad4 may affect the expression of fjx1, since fjx1 is abundantly expressed in the parental SW480 cells. If Notch signaling and fjx1 contribute to the tumorigenic phenotype, conditions that reverse this phenotype may also inhibit Notch signaling and fjx1 expression. As noted above, Smad4 expression suppresses tumorigenicity, increases expression of E-cadherin, and decreases expression of claudin 1 and ZEB-1. The inventors also observed that expression of fjx is significantly reduced in Smad4 expressing SW480 cells (FIG. 23). At present, they do not know whether this apparent reduction in fjx1 expression is due to decreased Notch signaling or through a separate mechanism.

Summary. The inventors have developed evidence that fjx1 is a colorectal cancer associated gene, expression of which is associated with poor patient survival. Notch signaling likely has a role in the regulation of fjx1 expression. Several lines of evidence in the published literature implicate Notch signaling as important in colorectal cancer, although its roles and impact on tumor phenotype are incompletely understood. Notch, planar cell polarity-associated genes and TGF-β/BMP pathway gene expression are all significantly modulated altered in association with increased fjx1 expression as determined by gene expression arrays of human colorectal cancers. They have now developed a highly sensitive anti-FJX1 antibody that recognizes both mouse and human forms of the protein and which will facilitate the completion of all of our specific aims. Taken together, these findings suggest that a complex interaction of FJX1, Notch signaling and BMP/Smad signaling that likely have important effects on determining colon cancer cell phenotype in a potentially regulated manner. Finally, inhibition of COX2 with Celebrex® in a clinical trial resulted in decreased mRNA expression fjx1. Since COX2 activity and its products such as PGE2 and other prostaglandins play important roles in cancer cell survival, EMT and angiogenesis, this may link both FJX1 and Notch signaling to these important roles in cancer.

\* \* \*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference:

U.S. Pat. No. 4,196,265
U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,873,191
U.S. Pat. No. 4,879,236
U.S. Pat. No. 4,883,750
U.S. Pat. No. 4,952,500
U.S. Pat. No. 5,217,879
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,464,765
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,824,544
U.S. Pat. No. 5,830,725
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,871,986
U.S. Pat. No. 5,879,934
U.S. Pat. No. 5,888,502
U.S. Pat. No. 5,925,565
U.S. Pat. No. 5,928,906
U.S. Pat. No. 5,932,210
U.S. Pat. No. 5,935,819
U.S. Pat. No. 5,945,100
U.S. Pat. No. 5,955,331
U.S. Pat. No. 5,981,274
U.S. Pat. No. 5,994,136
U.S. Pat. No. 5,994,624
U.S. Pat. No. 5,994,136
U.S. Pat. No. 5,994,624
U.S. Pat. No. 6,013,516
EPO 0273085
EPO 320 308
EPO 329 822
GB Appn. 2 202 328
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 9217598
PCT Appln. WO 94/09699
PCT Appln. WO 95/06128

Almendro et al., *J. Immunol.*, 157(12):5411-5421, 1996.
Amado and Chen, *Science*, 285(5428):674-676, 1999.
Angel et al., *Cell*, 49:729, 1987b.
Angel et al., *Mol. Cell. Biol.*, 7:2256, 1987a.
Armentano et al., *Proc. Natl. Acad. Sci. USA*, 87(16):6141-6145, 1990.
Artavanis-Tsakonas et al., *Science*, 284:770-776, 1999.
Atchison and Perry, *Cell*, 46:253, 1986.
Atchison and Perry, *Cell*, 48:121, 1987.
Ausubel et al., *In: Current Protocols in Molecular Biology*, John, Wiley & Sons, Inc, New York, 1994.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Bates, *Mol. Biotechnol.*, 2(2):135-145, 1994.
Batra et al., *Am. J. Respir. Cell Mol. Biol.*, 21(2):238-245, 1999.
Battraw and Hall, *Theor. App. Genet.*, 82(2):161-168, 1991.
Bellus, *J. Macromol. Sci. Pure Appl. Chem.*, A31(1): 1355-1376, 1994.
Berkhout et al., *Cell*, 59:273-282, 1989.
Bett et al., *J. Virololgy*, 67(10):5911-5921, 1993.
Bhattacharjee et al., *J. Plant Bioch. Biotech.*, 6(2):69-73. 1997.
Bilbao et al., *Transplant Proc.*, 31(1-2):792-793, 1999.
Blackwell et al., *Arch. Otolaryngol. Head. Neck Surg.*, 125 (8):856-863, 1999.
Blanar et al., *EMBO J*, 8:1139, 1989.
Blomer et al., *J. Virol.*, 71(9):6641-6649, 1997.
Bodine and Ley, *EMBO J*, 6:2997, 1987.
Boshart et al., *Cell*, 41:521, 1985.
Bosze et al., *EMBO J*, 5(7):1615-1623, 1986.
Braddock et al., *Cell*, 58:269, 1989.
Brinster et al., *Proc. Natl. Acad. Sci. USA*, 82(13):4438-4442, 1985. Levine, *Cell*, 88:323-331, 1997.
Buckles et al., *Development*, 128:3533-3542, 2001.

Bulla and Siddiqui, *J. Virol.*, 62:1437, 1986.
Campbell and Villarreal, *Mol. Cell. Biol.*, 8:1993, 1988.
Campbell et al., *Am. Rev. Respir. Dis.*, 130(3):417-423, 1984.
Campere and Tilghman, *Genes and Dev.*, 3:537, 1989.
Campo et al., *Nature*, 303:77, 1983.
Capaldi et al., *Biochem. Biophys. Res. Comm.*, 76:425, 1977.
Caplen et al., *Gene Ther.*, 6(3):454-459, 1999.
Carbonelli et al., "*FEMS Microbiol Lett.* 177(1):75-82, 1999.
Case et al., *Proc. Natl. Acad. Sci. USA*, 96(6):2988-2893, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.* 7:2745-2752, 1987.
Chen et al., *Genes Dev.*, 10:2438-2451, 1996.
Chillon et al., *J. Virol.*, 73(3):2537-2540, 1999.
Cho et al., *Biotechniques*, 30:562-572, 2001.
Choi et al., *Cell*, 53:519, 1988.
Christou et al., *Proc. Natl. Acad. Sci. USA*, 84(12):3962-3966, 1987.
Clay et al., *Pathol. Oncol. Res.*, 5(1):3-15, 1999.
Cocea, *Biotechniques*, 23(5):814-816, 1997.
Coffey et al., *Science*, 282(5392):1332-1334, 1999.
Cohen et al., *J. Cell. Physiol.*, 5:75, 1987.
Cook et al., *Cell*, 27:487-496, 1981.
Costa et al., *Mol. Cell. Biol.*, 8:81, 1988.
Cripe et al., *EMBO J*, 6:3745, 1987.
Culotta and Hamer, *Mol. Cell. Biol.*, 9:1376, 1989.
Culver et al., *Science*, 256(5063):1550-1552, 1992.
Dandolo et al., *J. Virology*, 47:55-64, 1983.
De Villiers et al., *Nature*, 312(5991):242-246, 1984.
DeLuca et al., *J. Virol.*, 56(2):558-570, 1985.
Deng et al., *Cell*, 82:675-684, 1995.
Derby et al., *Hear Res.*, 134(1-2):1-8, 1999.
Deschamps et al., *Science*, 230:1174-1177, 1985.
D'Halluin et al., *Plant Cell*, 4(12):1495-1505, 1992.
Dhawan et al., *J. Clin. Invest.*, 115:1765-1776, 2005.
Dorai et al., *Int. J. Cancer*, 82(6):846-852, 1999.
Edbrooke et al., *Mol. Cell. Biol.*, 9:1908, 1989.
Edlund et al., *Science*, 230:912-916, 1985.
Engel and Kohn, *Front Biosci.*, 4:e26-33, 1999.
Fechheimer, et al., *Proc Natl. Acad. Sci. USA*, 84:8463-8467, 1987.
Feldman et al., *Semin. Interv. Cardiol.*, 1(3):203-208, 1996.
Feng and Holland, *Nature*, 334:6178, 1988.
Feng et al., *Nat. Biotechnol.*, 15(9):866-870, 1997.
Fernandez-Majada et al., *Proc. Natl. Acad. Sci. USA*, 104:276-281, 2007.
Firak and Subramanian, *Mol. Cell. Biol.*, 6:3667, 1986.
Fisher et al., *Virology*, 217(1):11-22, 1996.
Foder et al., *Science*, 251:767-773, 1991.
Foecking and Hofstetter, *Gene*, 45(1):101-105, 1986.
Forster and Symons, *Cell*, 49:211-220, 1987.
Fraley et al., *Proc. Natl. Acad. Sci. USA*, 76:3348-3352, 1979.
Fre et al., *Nature*, 435:964-968, 2005.
Freifelder, In: *Physical Biochemistry Applications to Biochemistry and Molecular Biology*, 2nd Ed. Wm. Freeman and Co., NY, 1982.
Frohman, In: *PCR Protocols. A Guide To Methods And Applications*, Academic Press, N.Y., 1990.
Fryer et al., *Genes Dev.*, 16(11):1397-1411, 2002.
Fujita et al., *Cell*, 49:357, 1987.
Fujiwara and Tanaka, *Nippon Geka Gakkai Zasshi*, 99(7):463-468, 1998.
Garoff and Li, *Curr. Opin. Biotechnol.*, 9(5):464-469, 1998.
Gamido et al., *J. Neurovirol.*, 5(3):280-288, 1999.
Gefter et al., *Somatic Cell Genet.*, 3:231-236, 1977.
Gerlach et al., *Nature (London)*, 328:802-805, 1987.
Ghosh and Bachhawat, In: *Liver Diseases, Targeted Diagnosis and Therapy Using Specific Receptors and Ligands*, Wu and Wu (Eds.), Marcel Dekker, New York, 87-104, 1991.
Gilles et al., *Cell*, 33:717, 1983.
Gloss et al., *EMBO J.*, 6:3735, 1987.
Gnant et al., *Cancer Res.*, 59(14):3396-403, 1999.
Gnant et al., *J. Natl. Cancer Inst.*, 91(20):1744-1750, 1999.
Godbout et al., *Mol. Cell. Biol.*, 8:1169, 1988.
Goding, In: *Monoclonal Antibodies: Principles and Practice*, 2d ed., Orlando, Fla., Academic Press, 60-61, 65-66, 71-74, 1986.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Prevec *Mol. Biotechnol.*, 3(3):207-220, 1995.
Graham and Van Der Eb, *Virology* 52:456-467, 1973
Greene et al., *Immunology Today*, 10:272, 1989
Grosschedl and Baltimore, *Cell*, 41:885, 1985.
Hacia et al., *Nature Genet.*, 14:441-449, 1996.
Haecker et al., *Hum. Gene Ther.*, 7(15):1907-1914, 1996.
Han et al., *Euro. J Surgical Oncology*, 25:194-198, 1999.
Hanahan and Weinberg, *Cell*, 100:57-70, 2000.
Harland and Weintraub, *J. Cell Biol.*, 101:1094-1099, 1985.
Harlow and Lane, In: *Antibodies: A laboratory Manual, Cold Spring Harbor Laboratories, Cold Spring Harbor, N.Y.*, 1988.
Haslinger and Karin, *Proc. Natl. Acad. Sci. USA*, 82:8572, 1985.
Hauber and Cullen, *J. Virology*, 62:673, 1988.
Hayashi et al., *Neurosci. Lett.*, 267(1):37-40, 1999.
He et al., *Plant Cell Reports*, 14 (2-3):192-196, 1994.
Hen et al., *Nature*, 321:249, 1986.
Hensel et al., *Lymphokine Res.*, 8:347, 1989.
Hermens and Verhaagen, *Prog. Neurobiol.*, 55(4):399-432, 1998.
Herr and Clarke, *Cell*, 45:461, 1986.
Hewitt et al., *J. Pathol.*, 192:446-454, 2000.
Hirochika et al., *J. Virol.*, 61:2599, 1987.
Hirsch et al., *Mol. Cell. Biol.*, 10:1959, 1990.
Hogan et al., In: Manipulating the Mouse Embryo: A Laboratory Manual, 2nd ed., Cold Spring Harbor Laboratory Press, 1994.
Holbrook et al., *Virology*, 157:211, 1987.
Holzer et al., *Virology*, 253(1):107-114, 1999.
Horlick and Benfield, *Mol. Cell. Biol.*, 9:2396, 1989.
Hou and Lin, *Plant Physiology*, 111: 166, 1996.
Howard et al., *Ann. NY Acad. Sci.*, 880:352-365, 1999.
Huang et al., *Cell*, 27:245, 1981.
Huard et al., *Neuromuscul Disord.*, 7(5):299-313, 1997.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imai et al., *J. Virol.*, 72(5):4371-4378, 1998.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis, et al., In: *PCR Protocols. A guide to Methods and Application*, Academic Press, Inc. San Diego, 1990.
Irie et al., *Antisense Nucleic Acid Drug Dev.*, 9(4):341-349, 1999.

Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jemal et al., *Cancer J. Clin.*, 55:10-30, 2005.
Jemal et al., *Cancer J. Clin.*, 56:106-130, 2006.
Jensen et al., *Nat. Genet.*, 24:36-44, 2000.
Johnson et al., IN: *Biotechnology And Pharmacy*, Pezzuto et al., (Eds.), Chapman and Hall, New York, 1993.
Johnson et al., *Mol. Cell. Biol.*, 9:3393, 1989.
Johnson et al., *Clin. Gastroenterol. Hepatol.*, 4(11):1358-1365, 2006.
Johnston et al., *J. Virol.*, 73(6):4991-5000, 1999.
Joyce, *Nature*, 338:217-244, 1989.
Kadesch and Berg, *Mol. Cell. Biol.*, 6:2593, 1986.
Kaeppler et al., *Plant Cell Reports*, 9:415-418, 1990.
Kaibuchi et al., *Annu. Rev. Biochem.*, 68:459-486, 1999.
Kaneda et al., *Science*, 243:375-378, 1989.
Karin et al., *Mol. Cell. Biol.*, 7:606, 1987.
Katinka et al., *Cell*, 20:393, 1980.
Kato et al., *J. Biol. Chem.*, 266(6):3361-3364, 1991.
Kaufman et al., *Surv. Opthalmol.*, 43Suppl 1:S91-97, 1999.
Kawamoto et al., *Mol. Cell. Biol.*, 8:267, 1988.
Kay, *Haemophilia*, 4(4):389-392, 1998.
Kiledjian et al., *Mol. Cell. Biol.*, 8:145, 1988.
Kim and Cech, *Proc. Natl. Acad. Sci. USA*, 84:8788-8792, 1987.
Klamut et al., *Mol. Cell. Biol.*, 10:193, 1990.
Klimatcheva et al., *Front Biosci.*, 4:D481-96, 1999.
Kluppel and Wrana, *Bioessays*, 27:115-118, 2005.
Koch et al., *Mol. Cell. Biol.*, 9:303, 1989.
Kohler and Milstein, *Eur. J. Immunol.*, 6:511-519, 1976.
Kohler and Milstein, *Nature*, 256:495-497, 1975.
Kohut et al., *Am. J. Physiol.*, 275(6 Pt 1):L1089-94, 1998.
Kooby et al., *FASEB J.*, 13(11):1325-1334, 1999.
Kopan and Ilagan, *Nat. Rev. Mol. Cell. Biol.*, 5(6):499-504, 2004.
Kornberg, In: *DNA Replication*, W. H. Freeman and Company, New York, 1992.
Kraus et al., *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Krisky et al., *Gene Ther*, 5(11):1517-1530, 1998a.
Krisky et al., *Gene Ther*, 5(12):1593-1603, 1998b.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86(4):1173-1177, 1989.
Kyte and Doolittle, *J. Mol. Biol.*, 157(1):105-132, 1982.
Lachmann and Efstathiou, *Clin. Sci. (Colch)*, 96(6):533-541, 1999.
Lafreniere and Rosenberg, *J. Natl. Cancer Inst.*, 76:309-322, 1986.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lazzeri, *Methods Mol. Biol.*, 49:95-106, 1995.
Lee et al., *J. Auton. Nerv. Syst.*, 74(2-3):86-90, 1997.
Lee et al., *Korean J. Genet.*, 11(2):65-72, 1989.
Lee et al., *Nature*, 294:228, 1981.
Lee et al., *Nucleic Acids Res.*, 12:4191-206, 1984.
Leibowitz et al., *Diabetes*, 48(4):745-753, 1999.
Leong and Karsan, *Blood*, 107:2223-2233, 2006.
Lesch, *Biol. Psychiatry*, 45(3):247-253, 1999.
Levenson et al., *Human Gene Therapy*, 9:1233-1236, 1998.
Levinson et al., *Nature*, 295:79, 1982.
Li et al., *Science*, 275:1943-1947, 1997.
Lin et al., *Mol. Cell. Biol.*, 10:850, 1990.
Lundstrom, *J. Recept. Signal Transduct. Res.*, 19(1-4):673-686, 1999.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Varmus, *Proc. Natl. Acad. Sci. USA*, 80:5866, 1983.
Marienfeld et al., *Gene Ther.*, 6(6):1101-1113, 1999.
Mastrangelo et al., *Cancer Gene Ther.*, 6(5):409-422 1999.
McNeall et al., *Gene*, 76:81, 1989.
Merrifield, *Science*, 232(4748):341-347 1986.
Michel and Westhof, *J. Mol. Biol.*, 216:585-610, 1990.
Miksicek et al., *Cell*, 46:203, 1986.
Miller et al., *Methods Enzymol.*, 217:581-599, 1993.
Miyatake et al., *Gene Ther.*, 6(4):564-572, 1999.
Moldawer et al., *Shock*, 12(2):83-101, 1999.
Mordacq and Linzer, *Genes and Dev.*, 3:760, 1989.
Moreau et al., *Nucl. Acids Res.*, 9:6047, 1981.
Moriuchi et al., *Cancer Res.*, 58(24):5731-5737, 1998.
Morrison et al., *J. Gen. Virol.*, 78(Pt 4):873-878, 1997.
Muesing et al., *Cell*, 48:691, 1987.
Muller et al., *Exp. Cell Res.*, 280:119-133, 2002.
Naldini et al., *Proc. Natl. Acad. Sci. USA*, 93(21):11382-11388, 1996.
Neumann et al., *Proc. Natl. Acad. Sci. USA*, 96(16):9345-9350, 1999.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987
Nomoto et al., *Gene*, 236(2):259-271, 1999.
Ohara et al., *Proc. Natl. Acad. Sci. USA*, 86:5673-5677, 1989.
Omirulleh et al., *Plant Mol. Biol.*, 21(3):415-28, 1993.
Ondek et al., *EMBO J.*, 6:1017, 1987.
Ong et al., *J. Biol. Chem.*, 281(8):5106-5119, 2006.
Ornitz et al., *Mol. Cell. Biol.*, 7:3466, 1987.
Palmiter et al., *Nature*, 300:611, 1982.
Parks et al., *J. Virol.*, 71(4):3293-8, 1997.
Pease et al., *Proc. Natl. Acad. Sci. USA*, 91:5022-5026, 1994.
Pech et al., *Mol. Cell. Biol.*, 9:396, 1989.
Pelletier and Sonenberg, *Nature*, 334:320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Petrof, *Eur. Respir. J*, 11(2):492-497, 1998.
Picard and Schaffner, *Nature*, 307:83, 1984.
Pignon J et al., *Hum. Mutat.*, 3(2):126-132, 1994.
Pinkert et al., *Genes and Dev.*, 1:268, 1987.
Polyak et al., *Genes Dev.*, 10:1945-1952, 1996.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Rabinovitch et al., *Diabetes*, 48(6):1223-1229, 1999.
Reddy et al., *J. Virol.*, 72(2):1394-1402, 1998.
Redondo et al., *Science*, 247:1225, 1990.
Reinhold-Hurek and Shub, *Nature*, 357:173-176, 1992.

Reisman and Rotter, *Mol. Cell. Biol.*, 9:3571, 1989.
Remington's Pharmaceutical Sciences, 15$^{th}$ ed., pages 624-652, Mack Publishing Company, Easton, Pa., 1980.
Remington's Pharmaceutical Sciences 15th Edition, 33:624-652, 1990
Resendez Jr. et al., *Mol. Cell. Biol.*, 8:4579, 1988.
Rhodes et al., *Methods Mol. Biol.*, 55:121-131, 1995.
Ripe et al., *Mol. Cell. Biol.*, 9:2224, 1989.
Rippe et al., "DNA-mediated gene transfer into adult rat hepatocytes in primary culture," *Mol. Cell Biol.*, 10:689-695, 1990.
Rittling et al., *Nuc. Acids Res.*, 17:1619, 1989.
Robbins and Ghivizzani, *Pharmacol. Ther.*, 80(1):35-47, 1998.
Robbins et al., *Proc. Natl. Acad. Sci. USA*, 95(17):10182-10187, 1998.
Robbins et al., *Trends Biotechnol.*, 16(1):35-40, 1998.
Rock et al., *Dev. Dyn.*, 234:602-612, 2005a.
Rock et al., *Dev. Dyn.*, 234:747-755, 2005b.
Rosen et al., *Cell*, 41:813, 1988.
Rubie et al., *Mol. Cell. Probes*, 19:101-109, 2005.
Sakai et al., *Genes and Dev.*, 2:1144, 1988.
Sambrook et al., *In: Molecular Cloning: A Laboratory Manual*, Vol. 1, Cold Spring Harbor Laboratory Press, Cold Spring Harbor, N.Y., Ch. 7, 7.19-17.29, 1989.
Sarver et al., *Science*, 247:1222-1225, 1990.
Satake et al., *J. Virology*, 62:970, 1988.
Sawai et al., *Mol. Genet. Metab.*, 67(1):36-42, 1999.
Scanlon et al., *Proc. Natl. Acad. Sci. USA*, 88:10591-10595, 1991.
Schaffner et al., *J. Mol. Biol.*, 201:81, 1988.
Schmidt et al., *Surgery*, 138(2):306-312, 2005.
Schwarte-Waldhoff et al., *Oncogene*, 18:3152-3158, 1999.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sheng et al., *J. Biol. Chem.*, 275:6628-6635, 2000.
Sherman et al., *Mol. Cell. Biol.*, 9:50, 1989.
Shichiri and Hirata, Faseb J., 15:(6):1044-1053, 2001.
Shiou et al., *Cancer Res.*, 67:1571-1579, 2007.
Shoemaker et al., *Nature Genetics*, 14:450-456, 1996.
Sleigh and Lockett, *J. EMBO*, 4:3831, 1985.
Smith, *Arch. Neurol.*, 55(8):1061-1064, 1998.
Spalholz et al., *Cell*, 42:183, 1985.
Spandau and Lee, *J. Virology*, 62:427, 1988.
Spandidos and Wilkie, *EMBO J.* 2:1193, 1983.
Steck et al., *Nat. Genet.*, 15:356-362, 1997.
Stein et al., *J. Biol. Chem.*, 279:48930-48940, 2004.
Stephens and Hentschel, *Biochem. J*, 248:1, 1987.
Stewart and Young, "Solid Phase Peptide Synthesis", 2d. ed., Pierce Chemical Co., 1984.
Stewart et al., *Gene Ther.*, 6(3):350-363, 1999.
Stuart et al., *Nature*, 317:828, 1985.
Sullivan and Peterlin, *Mol. Cell. Biol.*, 7:3315, 1987.
Suzuki et al., *Biochem. Biophys. Res. Commun.*, 252(3):686-690, 1998.
Swartzendruber and Lehman, *J. Cell. Physiology*, 85:179, 1975.
Takebe et al., *Mol. Cell. Biol.*, 8:466, 1988.
Tam et al., *J. Am. Chem. Soc.*, 105:6442, 1983.
Tanaka et al., *Oncogene*, 8:2253-2258, 1993.
Taniura et al., *J. Biol. Chem.*, 274:16242-16248, 1999.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor and Stark, *Oncogene*, 20:1803-1815, 2001.
Taylor et al., *J. Biol. Chem.*, 264:15160, 1989.
Thiesen et al., *J. Virology*, 62:614, 1988.
Timiryasova et al., *Int. J. Oncol.*, 14(5):845-854, 1999.
Timiryasova et al., *Oncol. Res.;* 11(3):133-144, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tsukada et al., *Plant Cell Physiol.*, 30(4)599-604, 1989.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
van Es and Clevers, *Trends Mol. Med.*, 11:496-502, 2005.
van Es et al., *Nature*, 435:959-963, 2005.
Vanderkwaak et al., *Gynecol. Oncol.*, 74(2):227-234, 1999.
Vannice and Levinson, *J. Virology*, 62:1305, 1988.
Vasseur et al., *Proc Natl. Acad. Sci. USA*, 77:1068, 1980.
Vogelstein et al., *Nature*, 408(6810):307-310, 2000.
Vogelstein, *Nature*, 348(6303):681-682, 1990.
Vooijs et al., *Development*, 134:535-544, 2007.
Wagner et al., *Science*, 260:1510-1513, 1990.
Walker et al., *Nucleic Acids Res.*, 20(7):1691-1696, 1992.
Wang and Calame, *Cell*, 47:241, 1986.
Wang et al., *Gynecol. Oncol.*, 71(2):278-287, 1998.
Weber et al., *Cell*, 36:983, 1984.
Weihl et al., *Neurosurgery*, 44(2):239-252, 1999.
Weinberg et al., *Biochemistry*, 28:8263-8269, 1989.
Weinberger et al., *Mol. Cell. Biol.*, 8:988, 1984.
White et al., *J. Virol.*, 73(4):2832-28340, 1999.
Wilson and Radtke, *FEBS Lett.*, 580:2860-2868, 2006.
Wilson, *J. Clin. Invest.*, 98(11):2435, 1996.
Winoto and Baltimore, *Cell*, 59:649, 1989.
Wong et al., *Gene*, 10:87-94, 1980.
Wu and Wallace, *Genomics*, 4:560-569, 1989.
Wu and Wu, *J. Biol. Chem.*, 262:4429-4432, 1987.
Wu et al., *Biochem. Biophys. Res. Commun.*, 233(1):221-226, 1997.
Wu, *Chung Hua Min Kuo Hsiao Erh Ko I Hsuch Hui Tsa Chih*, 39(5):297-300, 1998.
Yamada et al., *Proc. Natl. Acad. Sci. USA*, 96(7):4078-4083, 1999.
Yang and Liang, *Mol. Biotechnol.*, 3:197-208, 2004.
Yeung et al., *Gene Ther.*, 6(9):1536-1544, 1999.
Yoon et al., *J. Gastrointest. Surg.*, 3(1):34-48, 1999.
You et al., *Nature*, 435(7038):98-104, 2005.
Yu and Zhang, *Biochem. Biophys. Res. Commun.*, 331:851-858, 2005.
Yu et al., *Proc. Natl. Acad. Sci. USA*, 100:1931-1936, 2003.
Yu et al., *Proc. Natl. Acad. Sci. USA*, 96:14517-14522, 1999.
Yutzey et al., *Mol. Cell. Biol.*, 9:1397, 1989.
Zavadil et al., *Embo J.*, 23:1155-1165, 2004.
Zeidler et al., *Curr. Biol.* 9:1363-1372, 1999a.
Zeidler et al., *Genes Dev.*, 13:1342-1353, 1999b.
Zhao-Emonet et al., *Biochim. Biophys. Acta*, 1442(2-3):109-119, 1998.
Zheng et al., *J. Gen. Virol.*, 80(Pt 7):1735-1742, 1999.
Zhou et al., *Exp. Hematol*, 21:928-933, 1993.
Zufferey et al., *Nat. Biotechnol.*, 15(9):871-875, 1997.

What is claimed is:

1. A method of diagnosing colorectal cancer comprising:
   (a) obtaining a biological sample from a subject;
   (b) assessing said biological sample for the level of a FJX1 nucleic acid;
   (c) comparing the level of FJX1 nucleic acid observed in step (b) with a comparable sample from a normal subject; and
   (d) diagnosing said subject with elevated FJX1 nucleic acid level in said biological sample, as compared to the nucleic acid level of FJX1 in said comparable sample from said normal subject, as having colorectal cancer.

2. The method of claim 1, wherein said sample is a tissue sample.

3. The method of claim 2, wherein said tissue sample is a biopsy.

4. The method of claim 1, wherein said sample is a biological fluid sample.

5. The method of claim 4, wherein said biological fluid sample is lymph, plasma, urine, feces or blood.

6. The method of claim 1, wherein said nucleic acid is an mRNA.

* * * * *